(12) United States Patent
McDaniel et al.

(10) Patent No.: US 8,232,246 B2
(45) Date of Patent: Jul. 31, 2012

(54) ANTI-VIRAL COMPOUNDS

(75) Inventors: Keith F. McDaniel, Wauconda, IL (US); Dale J. Kempf, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/495,299

(22) Filed: Jun. 30, 2009

(65) Prior Publication Data
US 2010/0168384 A1 Jul. 1, 2010

(51) Int. Cl.
*A61K 38/00* (2006.01)
(52) U.S. Cl. .......................................................... 514/3.7
(58) Field of Classification Search ........................ None
See application file for complete search history.

(56) References Cited

U.S. PATENT DOCUMENTS

| | | | |
|---|---|---|---|
| 6,534,523 B1 | 3/2003 | Llinas-Brunet et al. |
| 6,608,027 B1 | 8/2003 | Tsantrizos et al. |
| 6,703,403 B2 | 3/2004 | Norbeck et al. |
| 6,867,185 B2 | 3/2005 | Campbell et al. |
| 6,921,753 B2 | 7/2005 | Mantell et al. |
| 6,995,174 B2 | 2/2006 | Wang et al. |
| 7,119,072 B2 | 10/2006 | Llinas-Brunet et al. |
| 7,157,424 B2 | 1/2007 | Chen et al. |
| 7,173,004 B2 | 2/2007 | McPhee et al. |
| 7,176,208 B2 | 2/2007 | Nakajima et al. |
| 7,189,844 B2 | 3/2007 | Gallou et al. |
| 7,368,452 B2 | 5/2008 | Nakajima et al. |
| 7,375,218 B2 | 5/2008 | Gallou |
| 7,491,794 B2 | 2/2009 | Blatt et al. |
| 7,504,378 B2 | 3/2009 | Llinas-Brunet et al. |
| 7,566,719 B2 | 7/2009 | Nakajima et al. |
| 7,601,709 B2 | 10/2009 | Miao et al. |
| 7,642,339 B2 | 1/2010 | Chaudhary et al. |
| 7,741,281 B2 | 6/2010 | Dandrea et al. |
| 7,763,584 B2 | 7/2010 | Wang et al. |
| 7,772,183 B2 | 8/2010 | Carini et al. |
| 7,829,665 B2 | 11/2010 | Blatt et al. |
| 2003/0181363 A1 | 9/2003 | Llinas-Brunet et al. |
| 2003/0224977 A1 | 12/2003 | Llinas-Brunet et al. |
| 2004/0002448 A1 | 1/2004 | Tsantrizos et al. |
| 2004/0038872 A1 | 2/2004 | Campbell et al. |
| 2004/0072243 A1 | 4/2004 | Sands et al. |
| 2004/0106559 A1 | 6/2004 | Wang et al. |
| 2004/0180815 A1 | 9/2004 | Nakajima et al. |
| 2004/0229776 A1 | 11/2004 | Chen et al. |
| 2004/0229777 A1 | 11/2004 | Cerreta et al. |
| 2004/0248779 A1 | 12/2004 | Dersch et al. |
| 2004/0266668 A1 | 12/2004 | Nakajima et al. |
| 2005/0049187 A1 | 3/2005 | Brandenburg et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0119168 A1* | 6/2005 | Venkatraman et al. ............ 514/9 |
| 2005/0143316 A1 | 6/2005 | Tu et al. |
| 2005/0153877 A1 | 7/2005 | Miao et al. |
| 2005/0153900 A1* | 7/2005 | Velazquez et al. .............. 514/18 |
| 2005/0164921 A1* | 7/2005 | Njoroge et al. .................... 514/9 |
| 2005/0192212 A1 | 9/2005 | Llinas-Brunet et al. |
| 2005/0209135 A1 | 9/2005 | Busacca et al. |
| 2005/0215423 A1 | 9/2005 | Brenner et al. |
| 2005/0267018 A1 | 12/2005 | Blatt et al. |
| 2005/0267151 A1 | 12/2005 | Busacca et al. |
| 2006/0009667 A1 | 1/2006 | Herweck et al. |
| 2006/0063915 A1 | 3/2006 | Gallou et al. |
| 2006/0063916 A1 | 3/2006 | Gallou |
| 2006/0089300 A1 | 4/2006 | Llinas-Brunet et al. |
| 2006/0122123 A1 | 6/2006 | Chaudhary et al. |
| 2006/0205638 A1 | 9/2006 | Busacca et al. |
| 2006/0257980 A1 | 11/2006 | Li |
| 2006/0258868 A1* | 11/2006 | Bailey et al. .................. 546/152 |
| 2006/0275366 A1 | 12/2006 | Malcolm et al. |
| 2006/0276405 A1 | 12/2006 | Albrecht |
| 2006/0276407 A1 | 12/2006 | Albrecht et al. |
| 2006/0281688 A1 | 12/2006 | Zhang et al. |
| 2007/0004635 A1 | 1/2007 | Albrecht et al. |
| 2007/0010431 A1 | 1/2007 | Malcolm et al. |
| 2007/0043180 A1 | 2/2007 | Zhan |
| 2007/0060510 A1 | 3/2007 | Nakajima et al. |
| 2007/0072809 A1 | 3/2007 | Cho et al. |
| 2007/0078081 A1 | 4/2007 | Casarez et al. |
| 2007/0093414 A1 | 4/2007 | Carini et al. |
| 2007/0099825 A1 | 5/2007 | D'andrea et al. |
| 2007/0161575 A1 | 7/2007 | Miao et al. |
| 2007/0179167 A1 | 8/2007 | Cottrell et al. |
| 2007/0237818 A1 | 10/2007 | Malcolm et al. |

(Continued)

FOREIGN PATENT DOCUMENTS

EP    1169339 A1    1/2002

(Continued)

OTHER PUBLICATIONS

Rönn R Exploration of acyl sulfonamides as carboxylic acid replacements in protease inhibitors of the hepatitis C virus full-length NS3, Bioorg Med Chem. Jan. 15, 2006;14(2):544-59.*

Barbato G., et al., "Inhibitor Binding Induces Active Site Stabilization of the Hcv Ns3 Protein Serine Protease Domain," The EMBO Journal, 2000, vol. 19 (6), pp. 1195-1206.

Bose Ajay K. et al., "Heterocyclic Compounds IV. Synthesis of Some Mono- and Diazaphenanthrene Derivatives (1)," Department of Chemistry and Chemical Engineering, Stevens Institute of Technology, Hoboken, New Jersey, 1971, pp. 1091-1094, vol. 8.

(Continued)

*Primary Examiner* — Cecilia J Tsang
*Assistant Examiner* — Thomas Heard
(74) *Attorney, Agent, or Firm* — Xu Zhang

(57) ABSTRACT

Compounds capable of inhibiting replication of the hepatitis C virus ("HCV") are described. This invention also relates to processes of making such compounds, compositions comprising such compounds, and methods of using such compounds to treat HCV infection.

3 Claims, No Drawings

U.S. PATENT DOCUMENTS

| | | |
|---|---|---|
| 2007/0243166 A1 | 10/2007 | Llinas-Brunet et al. |
| 2007/0258947 A1 | 11/2007 | Njoroge et al. |
| 2007/0281884 A1 | 12/2007 | Sun et al. |
| 2007/0281885 A1 | 12/2007 | Sun et al. |
| 2007/0287664 A1 | 12/2007 | Ralston, II et al. |
| 2007/0299078 A1 | 12/2007 | Niu et al. |
| 2008/0008681 A1 | 1/2008 | Niu et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0107623 A1 | 5/2008 | D'andrea et al. |
| 2008/0107624 A1 | 5/2008 | D'andrea et al. |
| 2008/0107625 A1 | 5/2008 | D'andrea et al. |
| 2008/0108632 A1 | 5/2008 | Lin et al. |
| 2008/0119461 A1* | 5/2008 | Sin et al. .............. 514/227.2 |
| 2008/0145334 A1 | 6/2008 | Wang et al. |
| 2008/0152622 A1 | 6/2008 | Nakajima et al. |
| 2008/0159982 A1 | 7/2008 | Wang et al. |
| 2008/0181868 A1 | 7/2008 | Sun et al. |
| 2008/0242835 A1 | 10/2008 | Shu |
| 2008/0267916 A1 | 10/2008 | Gai et al. |
| 2008/0267917 A1 | 10/2008 | Niu et al. |
| 2008/0269228 A1 | 10/2008 | Moore et al. |
| 2008/0269502 A1 | 10/2008 | Gantz et al. |
| 2008/0279821 A1 | 11/2008 | Niu et al. |
| 2008/0311077 A1 | 12/2008 | Chaudhary et al. |
| 2009/0005387 A1 | 1/2009 | Niu et al. |
| 2009/0035271 A1 | 2/2009 | Sun et al. |
| 2009/0036708 A1 | 2/2009 | Jia et al. |
| 2009/0041721 A1 | 2/2009 | Niu et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0124808 A1 | 5/2009 | Busacca et al. |
| 2009/0130059 A1 | 5/2009 | Sun et al. |
| 2009/0148407 A1 | 6/2009 | Blatt et al. |
| 2009/0155209 A1 | 6/2009 | Blatt et al. |
| 2009/0163706 A1 | 6/2009 | Hildbrand et al. |
| 2009/0169510 A1 | 7/2009 | Blatt et al. |
| 2009/0176858 A1 | 7/2009 | Niu et al. |
| 2009/0186869 A1 | 7/2009 | Cottell et al. |
| 2009/0257978 A1 | 10/2009 | Cho et al. |
| 2009/0269305 A1 | 10/2009 | Seiwert et al. |
| 2009/0285773 A1 | 11/2009 | Sun et al. |
| 2009/0286814 A1 | 11/2009 | Lin et al. |
| 2009/0286843 A1 | 11/2009 | Blatt et al. |
| 2009/0297472 A1 | 12/2009 | Wang et al. |
| 2009/0304629 A1 | 12/2009 | Miao et al. |
| 2009/0306085 A1 | 12/2009 | Petter et al. |
| 2009/0326194 A1 | 12/2009 | Busacca et al. |
| 2010/0015092 A1 | 1/2010 | Nakajima et al. |
| 2010/0018355 A1 | 1/2010 | Crawford |
| 2010/0036116 A1 | 2/2010 | Scalone et al. |
| 2010/0041591 A1 | 2/2010 | Niu et al. |
| 2010/0069294 A1 | 3/2010 | Petter et al. |
| 2010/0074890 A1 | 3/2010 | Hagel et al. |
| 2010/0099695 A1 | 4/2010 | Liverton et al. |
| 2010/0124545 A1 | 5/2010 | Zhang et al. |
| 2010/0150866 A1 | 6/2010 | Wang et al. |
| 2010/0196321 A1 | 8/2010 | Cooper et al. |

FOREIGN PATENT DOCUMENTS

| | | |
|---|---|---|
| EP | 1437362 A1 | 7/2004 |
| EP | 1455809 A2 | 9/2004 |
| EP | 1472278 A2 | 11/2004 |
| WO | WO0059929 A1 | 10/2000 |
| WO | WO03053349 A2 | 7/2003 |
| WO | WO03064455 A2 | 8/2003 |
| WO | WO03066103 A1 | 8/2003 |
| WO | WO2004030670 A1 | 4/2004 |
| WO | WO2004037855 A1 | 5/2004 |
| WO | WO2004039833 A1 | 5/2004 |
| WO | WO2004087741 A1 | 10/2004 |
| WO | WO2004089974 A1 | 10/2004 |
| WO | WO2004092203 A2 | 10/2004 |
| WO | WO2004093798 A2 | 11/2004 |
| WO | WO2004093915 A1 | 11/2004 |
| WO | WO2004094452 A2 | 11/2004 |
| WO | WO2005028501 A1 | 3/2005 |
| WO | WO2005037214 A2 | 4/2005 |
| WO | WO2005046712 A1 | 5/2005 |
| WO | WO2005051980 A1 | 6/2005 |
| WO | WO2005070955 A1 | 8/2005 |
| WO | WO2005090383 A2 | 9/2005 |
| WO | WO2005095403 A2 | 10/2005 |
| WO | WO2006005479 A2 | 1/2006 |
| WO | WO2006020276 A2 | 2/2006 |
| WO | WO2006033851 A1 | 3/2006 |
| WO | WO2006033878 A1 | 3/2006 |
| WO | WO2006096652 A2 | 9/2006 |
| WO | WO2006130552 A2 | 12/2006 |
| WO | WO2006130553 A2 | 12/2006 |
| WO | WO2006130607 A2 | 12/2006 |
| WO | WO2006130626 A2 | 12/2006 |
| WO | WO2006130627 A2 | 12/2006 |
| WO | WO2006130628 A2 | 12/2006 |
| WO | WO2006130686 A2 | 12/2006 |
| WO | WO2006130687 A2 | 12/2006 |
| WO | WO2006130688 A2 | 12/2006 |
| WO | WO2007001406 A2 | 1/2007 |
| WO | WO2007008657 A2 | 1/2007 |
| WO | WO2007009109 A2 | 1/2007 |
| WO | WO2007014919 A1 | 2/2007 |
| WO | WO2007014926 A1 | 2/2007 |
| WO | WO2007015824 A2 | 2/2007 |
| WO | WO2007016441 A1 | 2/2007 |
| WO | WO2007030656 A1 | 3/2007 |
| WO | WO2007044893 A2 | 4/2007 |
| WO | WO2007044933 A2 | 4/2007 |
| WO | WO2007056120 A1 | 5/2007 |
| WO | WO2007139585 A1 | 12/2007 |
| WO | WO2007143694 A2 | 12/2007 |
| WO | WO2008002924 A2 | 1/2008 |
| WO | WO2008019289 A2 | 2/2008 |
| WO | WO2008019303 A2 | 2/2008 |
| WO | WO2008021956 A2 | 2/2008 |
| WO | WO2008021960 A2 | 2/2008 |
| WO | WO2008022006 A2 | 2/2008 |
| WO | WO2008046860 A2 | 4/2008 |
| WO | WO2008051475 A2 | 5/2008 |
| WO | WO2008057208 A2 | 5/2008 |
| WO | WO2008057873 A2 | 5/2008 |
| WO | WO2008057875 A2 | 5/2008 |
| WO | WO2008057995 A2 | 5/2008 |
| WO | WO2008060927 A2 | 5/2008 |
| WO | WO2008064057 A1 | 5/2008 |
| WO | WO2008064061 A1 | 5/2008 |
| WO | WO2008070733 A2 | 6/2008 |
| WO | WO2008086161 A1 | 7/2008 |
| WO | WO2008095058 A1 | 8/2008 |
| WO | WO2008098368 A1 | 8/2008 |
| WO | WO2008101665 A1 | 8/2008 |
| WO | WO2008106130 A2 | 9/2008 |
| WO | WO2008128921 A1 | 10/2008 |
| WO | WO2008137779 A2 | 11/2008 |
| WO | WO2008141227 A1 | 11/2008 |
| WO | WO2009005676 A2 | 1/2009 |
| WO | WO2009005677 A2 | 1/2009 |
| WO | WO2009010804 A1 | 1/2009 |
| WO | WO2009014730 A1 | 1/2009 |
| WO | WO2009053828 A2 | 4/2009 |
| WO | WO2009073713 A1 | 6/2009 |
| WO | WO2009073719 A1 | 6/2009 |
| WO | WO2009073780 A1 | 6/2009 |
| WO | WO2009080542 A1 | 7/2009 |
| WO | WO2009082697 A1 | 7/2009 |
| WO | WO2009082701 A1 | 7/2009 |
| WO | WO2009137432 A1 | 11/2009 |
| WO | WO2009139792 A1 | 11/2009 |
| WO | WO2009140500 A1 | 11/2009 |
| WO | WO2009142842 A2 | 11/2009 |
| WO | WO2009146347 A1 | 12/2009 |
| WO | WO2010015545 A1 | 2/2010 |
| WO | WO2010021717 A2 | 2/2010 |

| WO | WO2010028236 A1 | 3/2010 |
| WO | WO2010033466 A1 | 3/2010 |
| WO | WO2010042834 A1 | 4/2010 |
| WO | WO2010048468 A1 | 4/2010 |
| WO | WO2010059937 A1 | 5/2010 |
| WO | WO2010077783 A1 | 7/2010 |
| WO | WO2010088394 A1 | 8/2010 |
| WO | WO2010135748 A1 | 11/2010 |

OTHER PUBLICATIONS

Bundgaard H., "Design of Pro Drugs," 1985, pp. 1-6.

Dymock B.W., "Emerging Therapies for Hepatitis C Virus Infection," Expert Opinion on Emerging Drugs, 2001, vol. 6 (1), pp. 13-42.

Eisch J.J., et al., "Studies in Nonpyridinoid Azaaromatic Systems. 7. Synthesis and Tautomeric Character of Cyclopenta[c]quinoline (Benzo[c][2]pyrindine) 1," Journal of Organic Chemistry, 1978, vol. 43 (1), pp. 2190-2196.

Ferraris D., et al., "Design and synthesis of poly ADP-ribose polymerase-1 inhibitors. 2. Biological evaluation of aza-5[H]-phenanthridin-6-ones as potent, aqueous-soluble compounds for the treatment of ischemic injuries," Journal of Medicinal Chemistry, 2003, vol. 46 (14), pp. 3138-3151.

Goudreau N., et al., "NMR Structural Characterization of Peptide Inhibitors Bound to the Hepatitis C Virus NS3 Protease: Design of a New P2 Substituent," Journal of Medicinal Chemistry, 2004, vol. 47 (1), pp. 123-132.

Greene T.W., et al., "Protection for the Amino group," Protective Groups in Organic Synthesis, 1999, Third Edition, pp. 494-653.

Hoover J.E, Remington's Pharmaceutical Sciences, Tbl of Cont, 1975.

International Search Report for corresponding PCT International Application No. PCT/US09/05082 dated Apr. 1, 2010.

Jacques et al., "Enantiomers, Racemates, and Resolutions," J. Wiley & Sons, Chapter 3, pp. 197-213, 1981.

Jaroch S., et al., "Fluorinated dihydroquinolines as potent n-NOS inhibitors," Bioorganic & Medicinal Chemistry Letters, 2004, vol. 14 (3), pp. 743-746.

Johansson A., et al., "Acyl Sulfonamides as Potent Protease Inhibitors of the Hepatitis C Virus Full-Length NS3 (Protease-Helicase/NTPase): A Comparative Study of Different C-Terminals," Bioorganic & Medicinal Chemistry, 2003, vol. 11 (12), pp. 2551-2568.

Kim J.L., et al., "Crystal Structure of the Hepatitis C Virus NS3 Protease Domain Complexed with a Synthetic NS4A Cofactor Peptide," Cell, 1996, vol. 87 (2), pp. 343-355.

Lieberman L., et al., eds., Pharmaceutical Dosage Forms, vol. 1, Marcel Dekker, Inc., 1980, Table of Contents.

Llinas-Brunet M., et al., "Peptide-Based Inhibitors of the Hepatitis C Virus Serine Protease," Bioorganic & Medicinal Chemistry Letters, 1998, vol. 8 (13), pp. 1713-1718.

Lu L., et al., "Mutations Conferring Resistance to a Potent Hepatitis C Virus Serine Protease Inhibitor in Vitro," Antimicrobial Agents and Chemotherapy, 2004, vol. 48 (6), pp. 2260-2266.

Nathalie Goudreau, et al., "The therapeutic potential of NS3 protease inhibitors in HCV infection," Expert Opin. Investig. Drugs, vol. 14, No. 9, 2005, 1129-1144.

Rancourt J., et al., "Peptide-Based Inhibitors of the Hepatitis C Virus NS3 Protease: Structure-Activity Relationship at the C-Terminal Position," Journal of Medicinal Chemistry, 2004, vol. 47 (10), pp. 2511-2522.

Ried Walter et al., "N-Heterocyclen nus Cycloalkenylamin-Isocyanat-bzw.-Isothiocyanat-Addukten," Liebigs Ann Chem., 1965, vol. 688, pp. 177-188.

Rigby J.H., et al., "Vinyl Isocyanates in Synthesis. [4+2] Cycloaddition Reactions with Benzyne Addends," Journal of Organic Chemistry, 1989, vol. 54, pp. 4019-4020.

Rosowsky Andre et al., "Pyrimido[4,5-c]isoquinolines. 1. Synthesis of the Parent Compound and Some 6-Substituted Derivatives (1)," The Children's Cancer Research Foundation and the Department of Biological Chemistry, Harvard Medical School, Boston, Massachusetts, 1974, pp. 1081-1084, vol. 11.

Tsantrizos Y.S., et al., "Macrocyclic Inhibitors of the NS3 Protease as Potential Therapeutic Agents of Hepatitis C Virus Infection," Angewandte Chemie International Edition, 2003, vol. 42 (12), pp. 1355-1360.

* cited by examiner

ANTI-VIRAL COMPOUNDS

TECHNICAL FIELD

The present invention relates to compounds useful for treating HCV infection.

BACKGROUND

The hepatitis C virus (HCV) is the principal cause of non-A, non-B hepatitis and is an increasingly severe public health problem both in the developed and developing world. HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects and viral elimination from the body is often inadequate. Therefore, there is a need for new drugs to treat HCV infection.

SUMMARY

The present invention features compounds of Formulae I, II, III and IV, and pharmaceutically acceptable salts thereof. These compounds and salts can inhibit the activities of HCV protease and therefore the replication of HCV. These compounds and salts can be particularly effective in inhibiting the replication of HCV mutants.

The present invention also features compositions comprising the compounds or salts of the present invention. The compositions can also include other therapeutic agents, such as HCV helicase inhibitors, HCV polymerase inhibitors, other HCV protease inhibitors, HCV NS5A inhibitors, CD81 inhibitors, cyclophilin inhibitors, or internal ribosome entry site (IRES) inhibitors.

The present invention further features methods of using the compounds or salts of the present invention to inhibit HCV replication. The methods comprise contacting cells infected with HCV virus with a compound or salt of the present invention, thereby inhibiting the replication of HCV virus in the cells.

In addition, the present invention features methods of using the compounds or salts of the present invention, or compositions comprising the same, to treat HCV infection. The methods comprise administering a compound or salt of the present invention, or a pharmaceutical composition comprising the same, to a patient in need thereof, thereby reducing the blood or tissue level of HCV virus in the patient.

The present invention also features use of the compounds or salts of the present invention for the manufacture of medicaments for the treatment of HCV infection.

Furthermore, the present invention features processes of making the compounds or salts of the invention.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art in light of the detailed description herein.

DETAILED DESCRIPTION

The invention features compounds of Formulae I, II, III and IV, and pharmaceutically acceptable salts thereof,

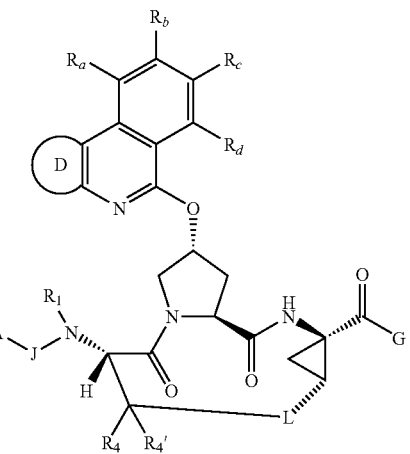

I

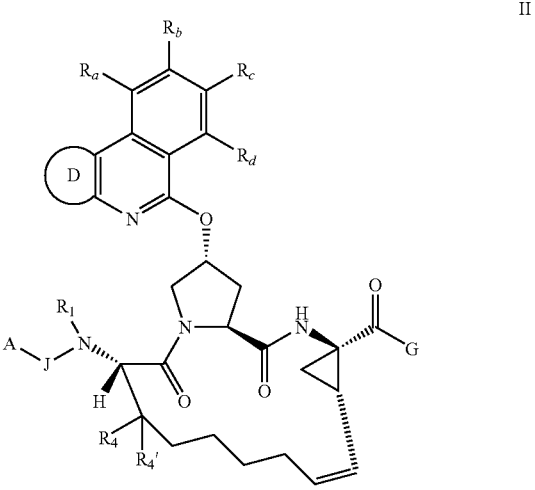

II

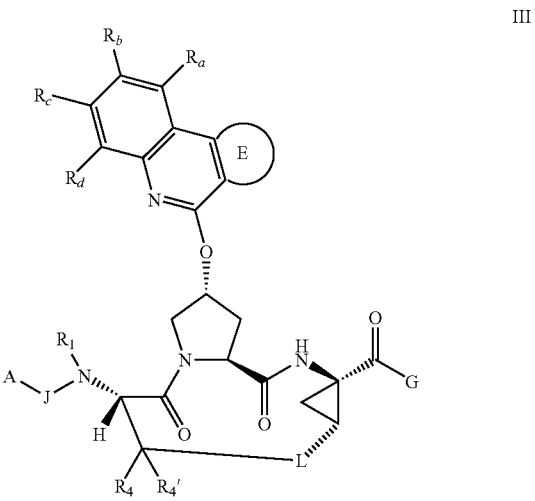

III

-continued

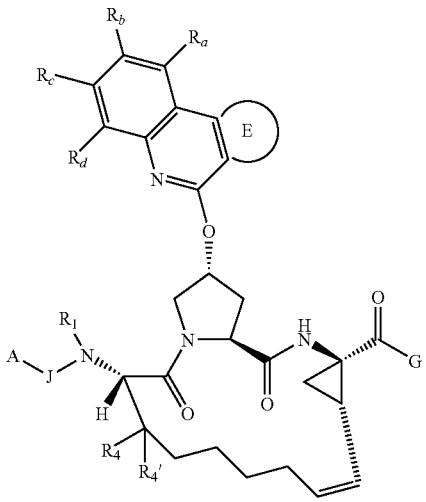

IV wherein:
D is a five, six or seven membered ring system containing one or two nitrogen and is optionally substituted with one or more R; or D is a 6- or 7-membered, non-aromatic carbocycle, and is optionally substituted with one or more R;

E is a 5-, 6- or 7-membered, non-aromatic ring system containing 0, 1 or 2 heteroatoms selected from nitrogen or oxygen, wherein E is optionally substituted with one or more R;

$R_a$, $R_b$, $R_c$, and $R_d$ are each independently selected from hydrogen, halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, $C_1$-$C_6$alkyl-S(O)—, $C_1$-$C_6$alkyl-S(O)$_2$—, $C_1$-$C_6$alkylamino, $C_1$-$C_6$alkylamide, $C_1$-$C_6$alkylamino$C_1$-$C_6$alkyl, $C_1$-$C_6$alkylcarbonyl, $C_1$-$C_6$alkylcarbonyloxy, $C_1$-$C_6$alkylcarbonyloxy$C_1$-$C_6$alkyl, $C_1$-$C_6$alkoxy$C_1$-$C_6$alkyl, $C_1$-$C_6$alkyl-S—$C_1$-$C_6$alkyl, $C_3$-$C_{10}$carbocycle, $C_3$-$C_{10}$carbocycle-O—, $C_7$-$C_{14}$alkylcarbocycle, or 5- to 12-membered heterocycle;

J is absent, —C(O)—, —O—C(O)—, or —N(A)-C(O)—;

A is independently selected at each occurrence from (1) hydrogen; or (2) $C_1$-$C_9$alkyl, $C_2$-$C_9$alkenyl, $C_2$-$C_9$alkynyl, $C_1$-$C_9$alkoxy, $C_3$-$C_{10}$carbocycle, $C_7$-$C_{14}$alkylcarbocycle, or 5-12 membered heterocycle, each of which is optionally substituted with one or more substituents independently selected from cyano, halogen, hydroxy, amino, carboxyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkylamino or $C_1$-$C_6$alkylamide; with the proviso that A-J- is not —COOH;

$R_1$ is hydrogen, $C_1$-$C_6$alkyl, $C_2$-$C_6$alkenyl, $C_2$-$C_6$alkynyl, or $C_3$-$C_7$carbocycle;

G is —O—$R_2$, —NH—SO$_2$—$R_2$, or —NH—C(O)—$R_2$, wherein $R_2$ is independently selected at each occurrence from hydrogen, $C_1$-$C_8$alkyl, $C_2$-$C_8$alkenyl, $C_2$-$C_8$alkynyl, $C_1$-$C_8$haloalkyl, $C_3$-$C_{14}$carbocycle optionally substituted with one or more R, $C_4$-$C_{16}$alkylcarbocycle optionally substituted with one or more R, or 5- to 7-membered heterocycle optionally substituted with one or more R;

L is $C_3$-$C_9$alkylene, $C_3$-$C_9$alkenylene or $C_3$-$C_9$alkynylene, each of which optionally contains 1 to 3 heteroatoms selected from O, S, S(O) or S(O)$_2$, and L is optionally substituted with one or more substituents independently selected from halogen, hydroxy, mercapto, cyano, nitro, amino, carboxyl, formyl, $C_1$-$C_6$alkyl, $C_2$-$C_6$alkenyl or $C_2$-$C_6$alkynyl;

$R_4$ and $R_4'$ are each independently hydrogen, halogen, $C_1$-$C_6$alkyl, $C_2$-$C_6$alkenyl or $C_2$-$C_6$alkynyl; and each R is independently selected at each occurrence from halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, $C_1$-$C_6$alkylamino, $C_1$-$C_6$alkylamino$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkoxy$C_1$-$C_6$alkyl, $C_1$-$C_6$alkyl-S—$C_1$-$C_6$alkyl, $C_3$-$C_8$carbocycle, $C_6$-$C_{16}$alkylcarbocycle, or 5- to 7-membered heterocycle.

As used herein throughout the present disclosure, a non-aromatic ring cannot be an aryl or heteroaryl ring. L preferably is a $C_5$-$C_7$ saturated or unsaturated chain (alkylene, alkenylene or alkynylene) optionally containing one oxygen. G preferably is —NH—SO$_2$—$R_2$, wherein $R_2$ is unsubstituted $C_3$-$C_7$cycloalkyl. A-J- preferably is —C(O)—$R_3$, wherein $R_3$ is 5-7 membered heterocycle optionally substituted with one or more halogen or $C_1$-$C_6$alkyl.

In one embodiment, the present invention features compounds of Formulae I, II, III and IV, and pharmaceutically acceptable salts thereof, wherein:

D is a five, six or seven membered ring system containing one or two nitrogen; or D is a 6- or 7-membered, non-aromatic carbocycle;

E is a 5-, 6- or 7-membered, non-aromatic ring system containing 0, 1 or 2 heteroatoms selected from nitrogen or oxygen;

$R_a$, $R_b$, $R_c$, and $R_d$ are each independently selected from hydrogen, halogen, hydroxy, mercapto, cyano, nitro, amino, $C_1$-$C_6$alkyl, $C_1$-$C_6$haloalkyl, $C_1$-$C_6$alkoxy, $C_1$-$C_6$haloalkoxy, $C_1$-$C_6$alkyl-S—, $C_1$-$C_6$alkylamino, $C_3$-$C_7$cycloalkyl, $C_6$-$C_{10}$aryl, $C_7$-$C_{14}$alkylaryl, or 5- to 7-membered monocyclic heterocycle;

A-J- is hydrogen; $C_1$-$C_6$alkyl or $C_3$-$C_7$cycloalkyl, each of which is optionally substituted with halogen; $C_1$-$C_6$alkoxy; —C(O)—$R_3$; —C(O)—O—$R_3$; or —C(O)—N($R_3$)$_2$;

each $R_3$ is independently $C_1$-$C_9$alkyl, $C_6$-$C_{10}$aryl, $C_7$-$C_{14}$alkylaryl, $C_3$-$C_7$cycloalkyl, or 5-7 membered heterocycle, each of which is independently optionally substituted with one or more substituents independently selected from halogen, $C_1$-$C_6$alkyl, $C_1$-$C_6$alkoxy, $C_1$-$C_6$haloalkyl or $C_1$-$C_6$haloalkoxy;

$R_1$ is hydrogen, $C_1$-$C_6$alkyl, or $C_3$-$C_7$cycloalkyl;

G is —O—$R_2$ or —NH—SO$_2$—$R_2'$, wherein $R_2$ is hydrogen, $C_1$-$C_6$alkyl, $C_3$-$C_7$cycloalkenyl, $C_6$-$C_{14}$aryl or $C_7$-$C_{16}$alkylaryl; and $R_2'$ is $C_1$-$C_8$alkyl, $C_4$-$C_{10}$alkylcycloalkyl, $C_3$-$C_7$cycloalkyl; or $R_2'$ is cyclopropyl or cyclobutyl and is optionally substituted with $C_1$-$C_4$alkyl, $C_2$-$C_5$alkenyl, $C_7$-$C_{16}$alkylaryl, $C_1$-$C_6$alkoxy, $C_1$-$C_6$alkoxy$C_1$-$C_6$alkyl, $C_5$-$C_7$cycloalkyl, $C_5$-$C_7$cycloalkenyl, $C_6$-$C_{10}$alkylcycloalkyl, halogen, $C_1$-$C_6$haloalkyl, cyano, or $C_1$-$C_6$haloalkoxy;

L is $C_3$-$C_9$alkylene, $C_3$-$C_9$alkenylene or $C_3$-$C_9$alkynylene, each of which optionally contains 1 to 3 heteroatoms selected from O, S, S(O) or S(O)$_2$; and $R_4$ and $R_4'$ are each independently hydrogen or methyl.

D and E are each independently optionally substituted with one or more R, and each R is independently selected at each occurrence from halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, or $C_1$-$C_6$alkylamino.

In another embodiment, the present invention features compounds of Formulae I, II, III and IV, and pharmaceutically acceptable salts thereof, wherein:

D is a five, six or seven membered ring system containing one or two nitrogen; or D is a 6- or 7-membered, non-aromatic carbocycle;

E is a 5-, 6- or 7-membered, non-aromatic ring system containing 0, 1 or 2 heteroatoms selected from nitrogen or oxygen;

$R_a$, $R_b$, $R_c$, and $R_d$ are hydrogen, halogen, $C_1$-$C_6$alkyl or $C_1$-$C_6$haloalkyl;

A-J- is $R_3$—C(O)— or $R_3$—O—C(O)—; wherein $R_3$ is independently $C_1$-$C_6$alkyl or 5-7 membered heterocycle, each of which is independently optionally substituted with one or more substituents independently selected from halogen, $C_1$-$C_6$alkyl, $C_1$-$C_6$alkoxy, $C_1$-$C_6$haloalkyl or $C_1$-$C_6$haloalkoxy;

$R_1$ is hydrogen or $C_1$-$C_6$alkyl;

G is —NH—SO$_2$—$R_2$', wherein $R_2$' is cyclopropyl or cyclobutyl and is optionally substituted with halogen, $C_1$-$C_4$alkyl or $C_2$-$C_5$alkenyl;

L is $C_3$-$C_9$alkylene, $C_3$-$C_9$alkenylene or $C_3$-$C_9$alkynylene; and $R_4$ and $R_4$' are each independently hydrogen or methyl.

D and E are each independently optionally substituted with one or more R, and each R is independently selected at each occurrence from halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, or $C_1$-$C_6$alkylamino.

In still another embodiment, the present invention features compounds of Formulae I, II, III and IV, and pharmaceutically acceptable salts thereof, wherein:

D is a five, six or seven membered ring system containing one or two nitrogen; or D is a 6- or 7-membered, non-aromatic carbocycle;

E is a 5-, 6- or 7-membered, non-aromatic ring system containing 0, 1 or 2 heteroatoms selected from nitrogen or oxygen;

$R_a$, $R_b$, $R_c$, and $R_d$ are each independently selected from hydrogen, halogen, hydroxy, mercapto, cyano, nitro, amino, $C_1$-$C_6$alkyl, $C_1$-$C_6$haloalkyl, $C_1$-$C_6$alkoxy, $C_1$-$C_6$haloalkoxy, $C_1$-$C_6$alkyl-S—, $C_1$-$C_6$alkylamino, $C_3$-$C_7$cycloalkyl, $C_6$-$C_{10}$aryl, $C_7$-$C_{14}$alkylaryl, or 5- to 7-membered monocyclic heterocycle;

A-J- is hydrogen; $C_1$-$C_6$alkyl or $C_3$-$C_7$cycloalkyl, each of which is optionally substituted with halogen; $C_1$-$C_6$alkoxy; —C(O)—$R_3$; —C(O)—O—$R_3$; or —C(O)—N($R_3$)$_2$;

each $R_3$ is independently $C_1$-$C_9$alkyl, $C_6$-$C_{10}$aryl, $C_7$-$C_{14}$alkylaryl, $C_3$-$C_7$cycloalkyl, or 5-7 membered heterocycle, each of which is independently optionally substituted with one or more substituents independently selected from halogen, $C_1$-$C_6$alkyl, $C_1$-$C_6$alkoxy, $C_1$-$C_6$haloalkyl or $C_1$-$C_6$haloalkoxy;

$R_1$ is hydrogen, $C_1$-$C_6$alkyl, or $C_3$-$C_7$cycloalkyl;

G is —O—$R_2$ or —NH—SO$_2$—$R_2$', wherein $R_2$ is hydrogen, $C_1$-$C_6$alkyl, $C_3$-$C_7$cycloalkenyl, $C_6$-$C_{14}$aryl or $C_7$-$C_{16}$alkylaryl; and $R_2$' is $C_1$-$C_8$alkyl, $C_4$-$C_{10}$alkylcycloalkyl, $C_3$-$C_7$cycloalkyl; or $R_2$' is cyclopropyl or cyclobutyl and is optionally substituted with $C_1$-$C_4$alkyl, $C_2$-$C_5$alkenyl, $C_7$-$C_{16}$alkylaryl, $C_1$-$C_6$alkoxy, $C_1$-$C_6$alkoxyC$_1$-$C_6$alkyl, $C_5$-$C_7$cycloalkyl, $C_5$-$C_7$cycloalkenyl, $C_6$-$C_{10}$alkylcycloalkyl, halogen, $C_1$-$C_6$haloalkyl, cyano, or $C_1$-$C_6$haloalkoxy; and $R_4$ and $R_4$' are each independently hydrogen or methyl.

D and E are each independently optionally substituted with one or more R, and each R is independently selected at each occurrence from halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, or $C_1$-$C_6$alkylamino.

In yet another embodiment, the present invention features compounds of Formulae I, II, III and IV, and pharmaceutically acceptable salts thereof, wherein:

D is a five, six or seven membered ring system containing one or two nitrogen; or D is a 6- or 7-membered, non-aromatic carbocycle;

E is a 5-, 6- or 7-membered, non-aromatic ring system containing 0, 1 or 2 heteroatoms selected from nitrogen or oxygen;

$R_a$, $R_b$, $R_c$, and $R_d$ are hydrogen, halogen, $C_1$-$C_6$alkyl or $C_1$-$C_6$haloalkyl;

A-J- is $R_3$—C(O)— or $R_3$—O—C(O)—; wherein $R_3$ is independently $C_1$-$C_6$alkyl or 5-7 membered heterocycle, each of which is independently optionally substituted with one or more substituents independently selected from halogen, $C_1$-$C_6$alkyl, $C_1$-$C_6$alkoxy, $C_1$-$C_6$haloalkyl or $C_1$-$C_6$haloalkoxy;

$R_1$ is hydrogen or $C_1$-$C_6$alkyl;

G is —NH—SO$_2$—$R_2$', wherein $R_2$' is cyclopropyl or cyclobutyl and is optionally substituted with halogen, $C_1$-$C_4$alkyl or $C_2$-$C_5$alkenyl; and $R_4$ and $R_4$' are each independently hydrogen or methyl.

D and E are each independently optionally substituted with one or more R, and each R is independently selected at each occurrence from halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, or $C_1$-$C_6$alkylamino.

In still yet another embodiment, the present invention features compounds of Formulae I, II, III and IV, and pharmaceutically acceptable salts thereof, wherein:

D is a five, six or seven membered ring system containing one or two nitrogen; or D is a 6- or 7-membered, non-aromatic carbocycle;

E is a 5-, 6- or 7-membered, non-aromatic ring system containing 0, 1 or 2 heteroatoms selected from nitrogen or oxygen;

$R_a$, $R_b$, $R_c$, and $R_d$ are hydrogen;

A-J- is $R_3$—C(O)—, and $R_3$ is 5-7 membered heterocycle optionally substituted with one or more halogen or $C_1$-$C_6$alkyl;

$R_1$ is hydrogen;

G is —NH—SO$_2$—$R_2$', wherein $R_2$' is cyclopropyl; and $R_4$ and $R_4$' are hydrogen.

D and E are each independently optionally substituted with one or more R, and each R is independently selected at each occurrence from halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, or $C_1$-$C_6$alkylamino.

In a further embodiment, the present invention features compounds of Formulae I, II, III and IV, and pharmaceutically acceptable salts thereof, wherein:

D is a six membered ring system containing one or two nitrogen;

E is a 6-membered, non-aromatic ring system containing 0, 1 or 2 heteroatoms selected from nitrogen or oxygen;

$R_a$, $R_b$, $R_c$, and $R_d$ are hydrogen;

A-J- is $R_3$—C(O)—, and $R_3$ is 5-7 membered heterocycle optionally substituted with one or more halogen or $C_1$-$C_6$alkyl;

$R_1$ is hydrogen;

G is —NH—$SO_2$—$R_2$', wherein $R_2$' is cyclopropyl; and $R_4$ and $R_4$' are hydrogen.

D and E are each independently optionally substituted with one or more R, and each R is independently selected at each occurrence from halogen, hydroxy, mercapto, cyano, nitro, amino, carboxyl, formyl, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$haloalkoxy, $C_1$-$C_6$alkyl-S—, or $C_1$-$C_6$alkylamino.

In still another embodiment, the present invention features compounds of Formulae I, II, III and IV, and pharmaceutically acceptable salts thereof, wherein:

D is a five, six or seven membered ring system which is not phenyl and which contains 0, 1, or 2 heteroatoms selected from oxygen or nitrogen;

E is a 5-, 6- or 7-membered, non-aromatic ring system containing 0, 1 or 2 heteroatoms selected from nitrogen or oxygen;

$R_a$, $R_b$, $R_c$, and $R_d$ are each independently selected from hydrogen, $C_{1-6}$alkyl, $C_{3-7}$cycloalkyl, $C_{1-6}$alkoxy, $C_{3-7}$cycloalkoxy, halo-$C_{1-6}$alkyl, $CF_3$, mono-or di-halo-$C_{1-6}$alkoxy, cyano, halo, thioalkyl, hydroxy, alkanoyl, $NO_2$, SH, amino, $C_{1-6}$alkylamino, di($C_{1-6}$)alkylamino, di($C_{1-6}$)alkylamide, carboxyl, ($C_{1-6}$)carboxyester, $C_{1-6}$alkylsulfone, $C_{1-6}$alkylsulfonamide, di($C_{1-6}$)alkyl(alkoxy)amine, $C_{6-10}$aryl, $C_{7-14}$alkylaryl, or a 5-7 membered monocyclic heterocycle;

$R_1$ is hydrogen, $C_{1-6}$alkyl, or $C_{3-7}$cycloalkyl;

$R_4$ and $R_4$' are each independently hydrogen or methyl;

L is a $C_{3-9}$ saturated or unsaturated chain, optionally containing one to three heteroatoms independently selected from O or S(O)m, wherein m is 0, 1 or 2;

A-J- is hydrogen; $C_{1-6}$alkyl or $C_{3-7}$cycloalkyl, each of which is optionally substituted with halo; alkoxy; —C(O)—$R_3$; —C(O)—O—$R_3$; or —C(O)—N($R_3$)$_2$;

each $R_3$ is independently $C_{1-9}$alkyl, optionally substituted with $C_{1-6}$alkoxy, $C_{3-7}$cycloalkoxy, halo-$C_{1-6}$alkoxy, cyano, halo, hydroxy, amino, $C_{1-6}$alkylamino, di($C_{1-6}$)alkylamino, di($C_{1-6}$)alkylamide, carboxyl, ($C_{1-6}$)carboxyester; $C_{6-10}$aryl; $C_{7-14}$alkylaryl; heterocyclyl; or $C_{3-7}$cycloalkyl optionally substituted with alkoxy, halo, or haloalkoxy; and G is OH, —O—$R_2$ or —NH—$SO_2$—$R_2$', wherein $R_2$ is $C_{1-6}$alkyl, unsaturated $C_{3-7}$cycloalkyl, $C_{6-14}$aryl or $C_{7-16}$alkylaryl; $R_2$' is $C_{1-8}$alkyl, $C_{4-10}$alkylcycloalkyl, unsubstituted $C_{3-7}$cycloalkyl; or $R_2$' is cyclopropyl or cyclobutyl optionally substituted with $C_{1-4}$alkyl, $C_{2-5}$alkenyl, $C_{7-16}$alkylaryl, alkoxy, alkoxyalkyl, $C_{5-7}$cycloalkyl, $C_{5-7}$cycloalkenyl, $C_{6-10}$alkylcycloalkyl, halo, haloalkyl, cyano, alkylcyano, halo alkoxy, or C(O)-Z; wherein the $C_{5-7}$cycloalkyl, the $C_{5-7}$cycloalkenyl, and the $C_{6-10}$alkylcycloalkyl are further optionally substituted with $C_{1-4}$alkyl or hydroxy; and wherein Z is selected from phenyl and —NHR$^N$; wherein R$^N$ is selected from $C_{1-6}$alkyl, heterocycle (e.g., 7-12 membered bicycle or 5-7 membered monocyclic heterocycle), and $C_{6-10}$aryl.

Preferably, D is a five, six or seven membered ring system containing 1, or 2 heteroatoms selected from oxygen or nitrogen; or D is a five, six or seven membered, non-aromatic carbocycle. More preferably, D is a five, six or seven membered ring system containing one or two nitrogen; or D is a 6- or 7-membered, non-aromatic carbocycle. Also preferably, D is a six membered ring system which is not phenyl and which contains 0, 1, or 2 heteroatoms selected from oxygen or nitrogen. Highly preferably, D is a six membered ring system containing 1 or 2 nitrogen; or D is a 6-membered, non-aromatic carbocycle. Preferably, E is a 5-, 6- or 7-membered, non-aromatic carbocycle. More preferably, E is a 6-membered non-aromatic carbocycle. L preferably is a $C_5$-$C_7$ saturated or unsaturated chain (alkylene, alkenylene or alkynylene) optionally containing one oxygen. G preferably is —NH—$SO_2$—$R_2$, wherein $R_2$ is unsubstituted $C_3$-$C_7$cycloalkyl. A-J- preferably is —C(O)—$R_3$, wherein $R_3$ is 5-7 membered heterocycle optionally substituted with one or more halogen or $C_1$-$C_6$alkyl.

In yet another embodiment, the present invention features compounds of Formulae I, II, III and IV, and pharmaceutically acceptable salts thereof, wherein:

D is a five, six or seven membered ring system which is not phenyl and which contains 0, 1, or 2 heteroatoms selected from oxygen or nitrogen;

E is a 5-, 6- or 7-membered, non-aromatic ring system containing 0, 1 or 2 heteroatoms selected from nitrogen or oxygen;

$R_a$, $R_b$, $R_c$, and $R_d$ are each independently selected from hydrogen, $C_{1-6}$alkyl, $C_{3-7}$cycloalkyl, $C_{1-6}$alkoxy, $C_{3-7}$cycloalkoxy, halo-$C_{1-6}$alkyl, $CF_3$, halo-$C_{1-6}$alkoxy, cyano, halo, thioalkyl, hydroxy, amino, $C_{1-6}$alkylamino, di($C_{1-6}$)alkylamino, di($C_{1-6}$)alkylamide, carboxyl, ($C_{1-6}$)carboxyester, $C_{1-6}$alkylsulfone, $C_{1-6}$alkylsulfonamide, di($C_{1-6}$)alkyl(alkoxy)amine, $C_{6-10}$aryl, $C_{1-14}$alkylaryl, or a 5-7 membered monocyclic heterocycle;

$R_1$ is hydrogen;

$R_4$ and $R_4$' are hydrogen;

L is a $C_{5-7}$ saturated or unsaturated chain, optionally containing one or two heteroatoms independently selected from O or S(O)m, wherein m is 0, 1 or 2;

A-J- is —C(O)—$R_3$, —C(O)—O—$R_3$, or —C(O)—NHR$_3$;

$R_3$ is $C_{1-9}$alkyl or heterocyclyl (preferably $R_3$ is $C_{1-9}$alkyl), optionally substituted with $C_{1-6}$alkoxy, cyano or halo; and G is OH or —NH—$SO_2$—$R_2$', wherein $R_2$' is $C_{1-8}$alkyl, $C_{4-10}$alkylcycloalkyl, unsubstituted $C_{3-7}$cycloalkyl, or cyclopropyl or cyclobutyl optionally substituted with $C_{1-4}$alkyl or $C_{7-16}$alkylaryl.

Preferably, D is a five, six or seven membered ring system containing 1, or 2 heteroatoms selected from oxygen or nitrogen; or D is a five, six or seven membered, non-aromatic carbocycle. More preferably, D is a five, six or seven membered ring system containing one or two nitrogen; or D is a 6- or 7-membered, non-aromatic carbocycle. Also preferably, D is a six membered ring system which is not phenyl and which contains 0, 1, or 2 heteroatoms selected from oxygen or nitrogen. Highly preferably, D is a six membered ring system containing 1 or 2 nitrogen; or D is a 6-membered, non-aromatic carbocycle. Preferably, E is a 5-, 6- or 7-membered, non-aromatic carbocycle. More preferably, E is a 6-membered non-aromatic carbocycle. L preferably is a $C_5$-$C_7$ saturated or unsaturated chain (alkylene, alkenylene or alkynylene) optionally containing one oxygen. G preferably is —NH—$SO_2$—$R_2$, wherein $R_2$ is unsubstituted $C_3$-$C_7$cycloalkyl. A-J- preferably is —C(O)—$R_3$, wherein $R_3$ is 5-7 membered heterocycle optionally substituted with one or more halogen or $C_1$-$C_6$alkyl.

In still yet another embodiment, the present invention features compounds of Formulae I, II, III and IV, and pharmaceutically acceptable salts thereof, wherein:

D is a five, six or seven membered ring system which is not phenyl and which contains 0, 1, or 2 heteroatoms selected from oxygen or nitrogen;

E is a 5-, 6- or 7-membered, non-aromatic ring system containing 0, 1 or 2 heteroatoms selected from nitrogen or oxygen;

$R_a$, $R_b$, $R_c$, and $R_d$ are each independently selected from hydrogen, $C_{1-6}$alkyl, $C_{3-7}$cycloalkyl, $C_{1-6}$alkoxy, $C_{3-7}$cycloalkoxy, halo-$C_{1-6}$alkyl, $CF_3$, mono-or di-halo-$C_{1-6}$alkoxy, cyano, halo, thioalkyl, hydroxy, alkanoyl, $NO_2$, SH, amino, $C_{1-6}$alkylamino, di($C_{1-6}$)alkylamino, di($C_{1-6}$)alkylamide, carboxyl, ($C_{1-6}$)carboxyester, $C_{1-6}$alkylsulfone, $C_{1-6}$alkylsulfonamide, di($C_{1-6}$)alkyl(alkoxy)amine, $C_{6-10}$aryl, $C_{1-14}$alkylaryl, or a 5-7 membered monocyclic heterocycle;

$R_1$ is hydrogen, $C_{1-6}$alkyl, or $C_{3-7}$cycloalkyl;

$R_4$ and $R_4'$ are each independently hydrogen or methyl;

L is a $C_{3-9}$ saturated or unsaturated chain, optionally containing one to three heteroatoms independently selected from O or S(O)m, wherein m is 0, 1 or 2;

A-J- is hydrogen; $C_{1-6}$alkyl or $C_{3-7}$cycloalkyl, each of which is optionally substituted with halo; alkoxy; —C(O)—$R_3$; —C(O)—O—$R_3$; or —C(O)—NHR$_3$;

each $R_3$ is independently $C_{1-9}$alkyl, optionally substituted with $C_{1-6}$alkoxy, $C_{3-7}$cycloalkoxy, halo-$C_{1-6}$alkoxy, cyano, halo, hydroxy, amino, $C_{1-6}$alkylamino, di($C_{1-6}$)alkylamino, di($C_{1-6}$)alkylamide, carboxyl, ($C_{1-6}$)carboxyester; $C_{6-10}$aryl; $C_{1-14}$alkylaryl; heterocyclyl; or $C_{3-7}$cycloalkyl; and G is OH, —O—$R_2$ or —NH—$SO_2$—$R_2'$, wherein $R_2$ is $C_{1-6}$alkyl, unsaturated $C_{3-7}$cycloalkyl, $C_{6-14}$aryl or $C_{7-16}$alkylaryl; $R_2'$ is $C_{1-8}$alkyl, $C_{4-10}$alkylcycloalkyl, unsubstituted $C_{3-7}$cycloalkyl; or $R_2'$ is cyclopropyl or cyclobutyl optionally substituted with $C_{1-4}$alkyl, $C_{7-16}$alkylaryl, alkoxy, halo, haloalkyl, cyano, alkylcyano or haloalkoxy.

Preferably, D is a five, six or seven membered ring system containing 1, or 2 heteroatoms selected from oxygen or nitrogen; or D is a five, six or seven membered, non-aromatic carbocycle. More preferably, D is a five, six or seven membered ring system containing one or two nitrogen; or D is a 6- or 7-membered, non-aromatic carbocycle. Also preferably, D is a six membered ring system which is not phenyl and which contains 0, 1, or 2 heteroatoms selected from oxygen or nitrogen. Highly preferably, D is a six membered ring system containing 1 or 2 nitrogen; or D is a 6-membered, non-aromatic carbocycle. Preferably, E is a 5-, 6- or 7-membered, non-aromatic carbocycle. More preferably, E is a 6-membered non-aromatic carbocycle. L preferably is a $C_5$-$C_7$ saturated or unsaturated chain (alkylene, alkenylene or alkynylene) optionally containing one oxygen. G preferably is —NH—$SO_2$—$R_2$, wherein $R_2$ is unsubstituted $C_3$-$C_7$cycloalkyl. A-J- preferably is —C(O)—$R_3$, wherein $R_3$ is 5-7 membered heterocycle optionally substituted with one or more halogen or $C_1$-$C_6$alkyl.

In some cases, L can a $C_{5-7}$ saturated or unsaturated chain optionally containing one to three heteroatoms independently selected from O or S(O)m; wherein m is 0, 1 or 2. For instance, L can be a $C_6$ saturated or unsaturated chain optionally containing one to three heteroatoms independently selected from O or S(O)m, wherein m is 0, 1 or 2. L can also be unsaturated. In one example, L has six carbon atoms. In another example, L has a structure selected from:

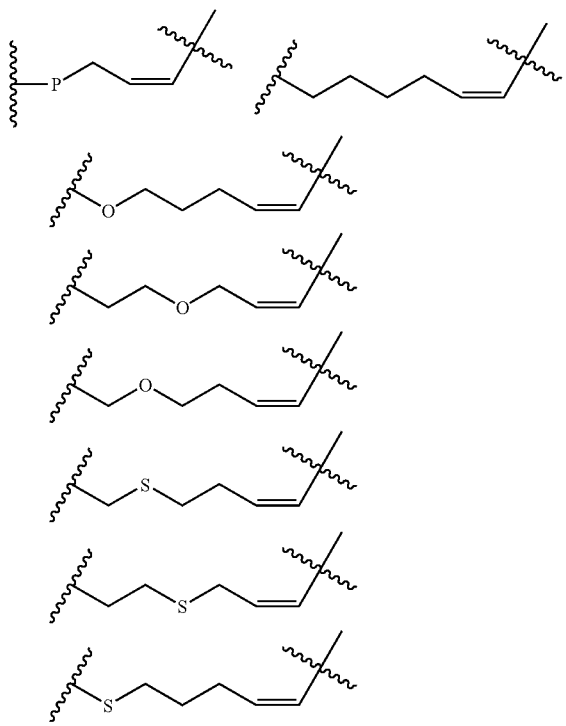

wherein P is a $C_3$ saturated chain optionally containing one heteroatom independently selected from O or S(O)m, where m is 0, 1 or 2.

In one embodiment, the present invention features compounds of Formulae I, II, III and IV, and pharmaceutically acceptable salts thereof, wherein:

D is a five, six or seven membered ring system which is not phenyl and which contains 0, 1, or 2 heteroatoms selected from oxygen or nitrogen;

E is a 5-, 6- or 7-membered, non-aromatic ring system containing 0, 1 or 2 heteroatoms selected from nitrogen or oxygen;

$R_a$, $R_b$, $R_c$, and $R_d$ are each independently selected from hydrogen, $C_{1-6}$alkyl, $C_{3-7}$cycloalkyl, $C_{1-6}$alkoxy, $C_{3-7}$cycloalkoxy, halo-$C_{1-6}$alkyl, $CF_3$, halo-$C_{1-6}$alkoxy, cyano, halo, thioalkyl, hydroxy, amino, $C_{1-6}$alkylamino, di($C_{1-6}$)alkylamino, di($C_{1-6}$)alkylamide, carboxyl, ($C_{1-6}$)carboxyester, $C_{1-6}$alkylsulfone, $C_{1-6}$alkylsulfonamide, di($C_{1-6}$)alkyl(alkoxy)amine, $C_{6-10}$aryl, $C_{1-14}$alkylaryl, or a 5-7 membered monocyclic heterocycle;

$R_1$ is hydrogen;

$R_4$ and $R_4'$ are hydrogen;

L is a $C_{5-7}$ saturated or unsaturated chain, optionally containing one to three heteroatoms independently selected from O or S(O)m, wherein m is 0, 1 or 2;

A-J- is —C(O)—$R_3$, —C(O)—O—$R_3$, or —C(O)—NHR$_3$;

$R_3$ is $C_{1-9}$alkyl or heterocyclyl (preferably $R_3$ is $C_{1-9}$alkyl), optionally substituted with $C_{1-6}$alkoxy, cyano or halo; and G is —NH—$SO_2$—$R_2'$, wherein $R_2'$ is $C_{1-8}$alkyl, $C_{4-10}$alkylcycloalkyl, unsubstituted $C_{3-7}$cycloalkyl; or cyclopropyl or cyclobutyl optionally substituted with $C_{1-4}$alkyl or $C_{7-16}$alkylaryl.

Preferably, D is a five, six or seven membered ring system containing 1, or 2 heteroatoms selected from oxygen or nitrogen; or D is a five, six or seven membered, non-aromatic carbocycle. More preferably, D is a five, six or seven membered ring system containing one or two nitrogen; or D is a 6- or 7-membered, non-aromatic carbocycle. Also preferably, D is a six membered ring system which is not phenyl and which contains 0, 1, or 2 heteroatoms selected from oxygen or nitrogen. Highly preferably, D is a six membered ring system containing 1 or 2 nitrogen; or D is a 6-membered, non-aromatic carbocycle. Preferably, E is a 5-, 6- or 7-membered, non-aromatic carbocycle. More preferably, E is a 6-membered non-aromatic carbocycle. In one example, $R_3$ is $C_{1-9}$alkyl or heterocyclyl (preferably $R_3$ is $C_{1-9}$alkyl) and is optionally substituted with halo; $R_2'$ is $C_{1-8}$alkyl or $C_{3-7}$cycloalkyl; $R_a$, $R_b$, $R_c$, and $R_d$ are each independently selected from hydrogen, $C_{1-6}$alkyl, $C_{3-7}$cycloalkyl, $C_{1-6}$alkoxy, $C_{3-7}$cycloalkoxy, halo-$C_{1-6}$alkyl, halo-$C_{1-6}$alkoxy, cyano, halo or di($C_{1-6}$)alkylamino; and L is selected from the following structures:

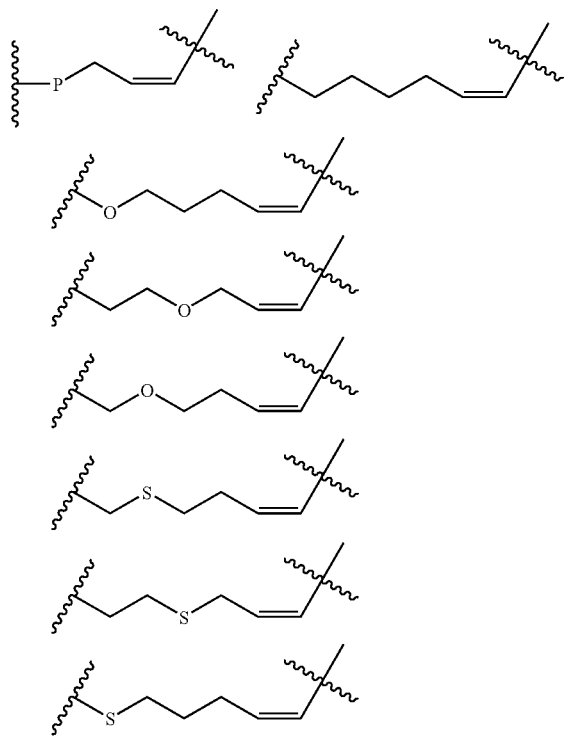

wherein P is a $C_3$ saturated chain optionally containing one heteroatom independently selected from O or S(O)m, where m is 0, 1 or 2. In another example, $R_3$ is $C_{1-9}$alkyl or heterocyclyl (preferably $R_3$ is $C_{1-9}$galkyl); $R_2'$ is cyclopropyl; $R_a$, $R_b$, $R_c$, and $R_d$ are each independently selected from hydrogen, methoxy or chloro; and L is selected from the following structures:

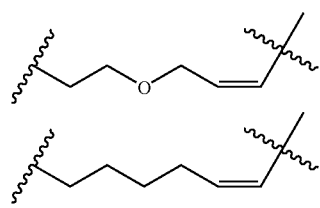

-continued

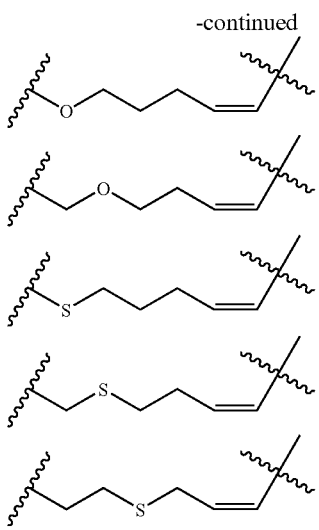

In still another example, $R_3$ is $C_{1-6}$alkyl; $R_2'$ is cyclopropyl; $R_a$, $R_b$, $R_c$, and $R_d$ are hydrogen; or each independently selected from hydrogen, $C_{1-6}$alkyl, $C_{3-7}$cycloalkyl, $C_{1-6}$alkoxy, $C_{3-7}$cycloalkoxy, halo-$C_{1-6}$alkyl, halo-$C_{1-6}$alkoxy, cyano, halo or di($C_{1-6}$)alkylamino; and L is selected from the following structures:

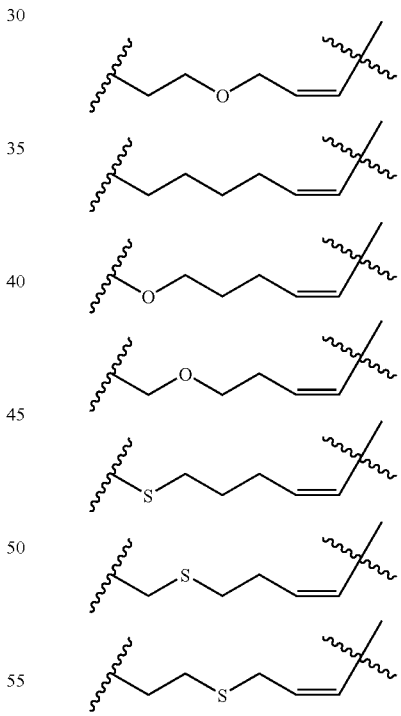

The compounds of the present invention can be used in the form of salts. Depending on the particular compound, a salt of a compound may be advantageous due to one or more of the salt's physical properties, such as enhanced pharmaceutical stability under certain conditions or desired solubility in water or oil. In some instances, a salt of a compound may be useful for the isolation or purification of the compound.

Where a salt is intended to be administered to a patient, the salt preferably is pharmaceutically acceptable. Pharmaceutically acceptable salts include, but are not limited to, acid addition salts, base addition salts, and alkali metal salts.

Pharmaceutically acceptable acid addition salts may be prepared from inorganic or organic acids. Examples of suitable inorganic acids include, but are not limited to, hydrochloric, hydrobromic, hydroionic, nitric, carbonic, sulfuric, and phosphoric acid. Examples of suitable organic acids include, but are not limited to, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts include, but are not limited to, metallic salts and organic salts. Non-limiting examples of suitable metallic salts include alkali metal (group Ia) salts, alkaline earth metal (group IIa) salts, and other pharmaceutically acceptable metal salts. Such salts may be made, without limitation, from aluminum, calcium, lithium, magnesium, potassium, sodium, or zinc. Non-limiting examples of suitable organic salts can be made from tertiary amines and quaternary amine, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as alkyl halides (e.g., methyl, ethyl, propyl, butyl, decyl, lauryl, myristyl, and stearyl chlorides/bromides/iodides), dialkyl sulfates (e.g., dimethyl, diethyl, dibuytl, and diamyl sulfates), aralkyl halides (e.g., benzyl and phenethyl bromides), and others.

The compounds or salts of the present invention may exist in the form of solvates, such as with water (i.e., hydrates), or with organic solvents (e.g., with methanol, ethanol or acetonitrile to form, respectively, methanolate, ethanolate or acetonitrilate).

The compounds or salts of the present invention may also be used in the form of prodrugs. Some prodrugs are aliphatic or aromatic esters derived from acidic groups on the compounds of the invention. Others are aliphatic or aromatic esters of hydroxyl or amino groups on the compounds of the invention. Phosphate prodrugs of hydroxyl groups are preferred prodrugs.

The compounds of the invention may comprise asymmetrically substituted carbon atoms known as chiral centers. These compounds may exist, without limitation, as single stereoisomers (e.g., single enantiomers or single diastereomer), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free," it means that at least 80% of the compound in a composition is the described stereoisomer; preferably, at least 90% of the compound in a composition is the described stereoisomer; and more preferably, at least 95%, 96%, 97%, 98% or 99% of the compound in a composition is the described stereoisomer. Where the stereochemistry of a chiral carbon is not specified in the chemical structure of a compound, the chemical structure is intended to encompass compounds containing either stereoisomer of the chiral center.

Individual stereoisomers of the compounds of this invention can be prepared using a variety of methods known in the art in light of the present invention. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art in light of the present invention. Chromatographic resolution of enantiomers can be accomplished by using chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et at., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The invention encompasses each conformational isomer of these compounds and mixtures thereof.

Certain compounds of the invention may also exist in zwitterionic form and the invention encompasses each zwitterionic form of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables. Unless otherwise specified, each variable within such a formula is defined independently of any other variable, and any variable that occurs more than one time in a formula is defined independently at each occurrence. If moieties are described as being "independently" selected from a group, each moiety is selected independently from the other. Each moiety therefore can be identical to or different from the other moiety or moieties.

The number of carbon atoms in a hydrocarbyl moiety can be indicated by the prefix "$C_X$-$C_Y$" or "$C_{X\text{-}Y}$" where X is the minimum and Y is the maximum number of carbon atoms in the moiety. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. For another instance, $C_7$-$C_{16}$alkylcarbocycle means an alkylcarbocycle containing from 7 to 16 carbon atoms.

Unless otherwise specified, when a linking element links two other elements in a depicted chemical structure, the leftmost-described component of the linking element is bound to the left element in the depicted structure, and the rightmost-described component of the linking element is bound to the right element in the depicted structure.

If a linking element in a depicted structure is absent or is a bond, then the element left to the linking element is joined directly to the element right to the linking element via a covalent bond. For example, if a chemical structure is depicted as A-J- and J is absent or a bond, then the chemical structure will be A-.

When a chemical formula is used to describe a moiety, the dash indicates the portion of the moiety that has the free valence.

If a moiety is described as being "optionally substituted", the moiety may be either substituted or unsubstituted. If a moiety is described as being optionally substituted with up to a particular number of non-hydrogen radicals, that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions. To illustrate, tetrazolyl (which has only one substitutable position) will be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" means a straight or branched hydrocarbyl chain containing one or more double bonds. Each carbon-carbon double bond may have either cis or trans geometry within the alkenyl moiety, relative to groups substituted on the double bond carbons. Non-limiting examples of alkenyl groups include ethenyl (vinyl), 2-propenyl, 3-propenyl, 1,4-pentadienyl, 1,4-butadienyl, 1-butenyl, 2-butenyl, and 3-butenyl.

The term "alkenylene" refers to a divalent unsaturated hydrocarbyl chain which may be linear or branched and which has at least one carbon-carbon double bond. Non-limiting examples of alkenylene groups include —C(H)=C(H)—, —C(H)=C(H)—CH$_2$—, —C(H)=C(H)—CH$_2$—CH$_2$—, —CH$_2$—C(H)=C(H)—CH$_2$—, —C(H)=C(H)—CH(CH$_3$)—, and —CH$_2$—C(H)=C(H)—CH(CH$_2$CH$_3$)—.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkylene" denotes a divalent saturated hydrocarbyl chain which may be linear or branched. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "alkynylene" refers to a divalent unsaturated hydrocarbon group which may be linear or branched and which has at least one carbon-carbon triple bonds. Representative alkynylene groups include, by way of example, —C≡C—, —C≡C—CH$_2$—, —C≡C—CH$_2$—CH$_2$—, —CH$_2$—C≡C—CH$_2$—, —C≡C—CH(CH$_3$)—, and —CH$_2$—C≡C—CH(CH$_2$CH$_3$)—.

The term "carbocycle" or "carbocyclic" or "carbocyclyl" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. A carbocyclyl may be, without limitation, a single ring, two fused rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocycle group can be attached to the parent molecular moiety through any substitutable carbon ring atom.

The term "carbocyclylalkyl" refers to a carbocyclyl group appended to the parent molecular moiety through an alkylene group. For instance, $C_3$-$C_6$carbocyclyl$C_1$-$C_6$alkyl refers to a $C_3$-$C_6$carbocyclyl group appended to the parent molecular moiety through $C_1$-$C_6$alkylene.

The term "cycloalkenyl" refers to a non-aromatic, partially unsaturated carbocyclyl moiety having zero heteroatom ring member. Representative examples of cycloalkenyl groups include, but are not limited to, cyclobutenyl, cyclopentenyl, cyclohexenyl, and octahydronaphthalenyl.

The term "cycloalkyl" refers to a saturated carbocyclyl group containing zero heteroatom ring member. Non-limiting examples of cycloalkyls include cyclopropyl, cyclobutyl, cyclopentyl, cyclohexyl, cycloheptyl, cyclooctyl, decalinyl and norpinanyl.

The prefix "halo" indicates that the substituent to which the prefix is attached is substituted with one or more independently selected halogen radicals ("halo"). For example, "$C_1$-$C_6$haloalkyl" means a $C_1$-$C_6$alkyl substituent wherein one or more hydrogen atoms are replaced with independently selected halogen radicals. Non-limiting examples of $C_1$-$C_6$haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "heterocycle" or "heterocyclo" or "heterocyclyl" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocycle may be, without limitation, a single ring, two fused rings, or bridged or spiro rings. A heterocycle group can be linked to the parent molecular moiety via any substitutable carbon or nitrogen atom(s) in the group.

A heterocyclyl may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl"), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, and diazepinyl.

A heterocyclyl may also be, without limitation, a bicycle containing two fused rings, such as, for example, naphthyridinyl (including [1,8] naphthyridinyl, and [1,6] naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), benzimidazolyl, phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), and tetrahydroisoquinolinyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

"Alkyoxy" or "alkoxy" means an alkyl group attached to the parent molecular through an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

"Thialkyl" means an alkyl group attached to the parent molecule through S (i.e., alkyl-S—).

"Alkylamide" means an amide mono-substituted with an alkyl, such as

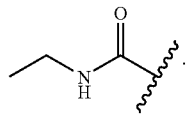

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The terms "leaving group" or "LG" refer to any group that leaves in the course of a chemical reaction involving the group and includes but is not limited to halogen, brosylate, mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The terms "amino protecting group," "N-protecting group," or "N-protected" refer to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The terms "halo" and "halogen" refer to an atom selected from fluorine, chlorine, bromine and iodine.

The compounds and processes of the present invention will be better understood in connection with the following synthetic schemes that illustrate the methods by which the compounds of the invention may be prepared. Other suitable methods may also be used to prepare the compounds of the present invention, as appreciated by those skilled in the art in light to the present invention.

All variables in the structures in the schemes are as defined hereinabove unless specified otherwise.

Scheme 1
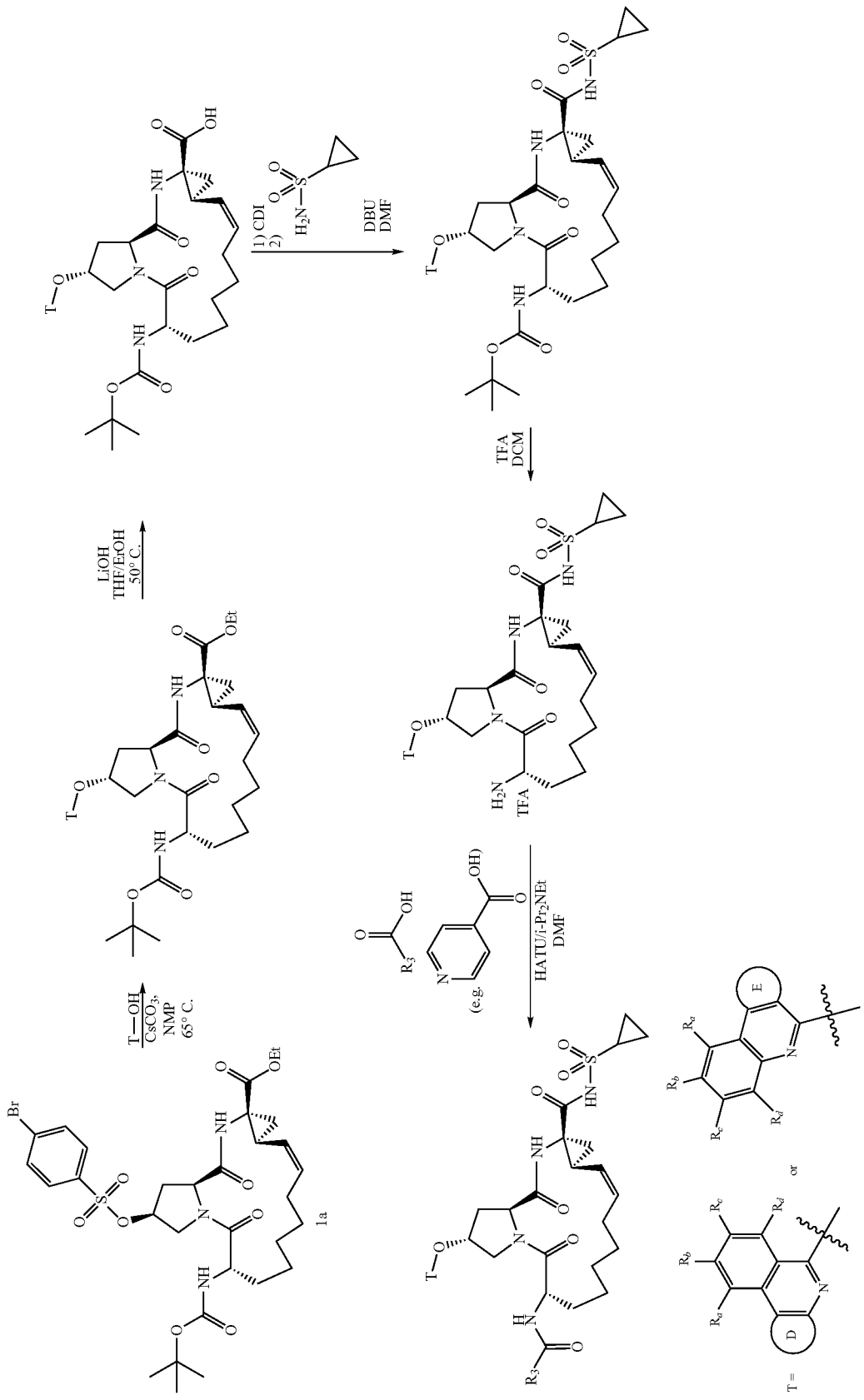

Scheme 1 describes the synthesis of various compounds of the invention. The starting material is displaced at the leaving groups by reaction with a nucleophile to provide a nucleophile substituted macrocycle. Base hydrolysis of the ester to the acid is followed by coupling of a sulfonamide derivative. The protected nitrogen may then be deprotected and substituted with another group, wherein D, E, $R_3$, $R_a$, $R_b$, $R_c$, and $R_d$ are as described hereinabove.

In one aspect, the present invention features a method of manufacturing a compound of Formula I or III, comprising the step of reacting a compound of formula V with T-OH,

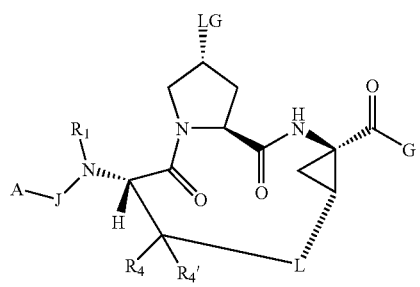

V wherein:
LG is a leaving group;
T is

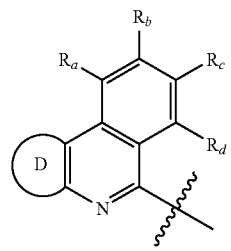

(for making Formula I) or

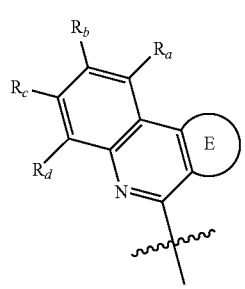

(for making Formula III); and
A, J, G, L, $R_1$, $R_4$, $R_4'$, D. E, $R_a$, $R_b$, $R_c$, and $R_d$ are as described hereinabove.

In another aspect, the present invention features a method of manufacturing a compound of Formula II or IV, comprising the step of reacting a compound of formula VI with T-OH,

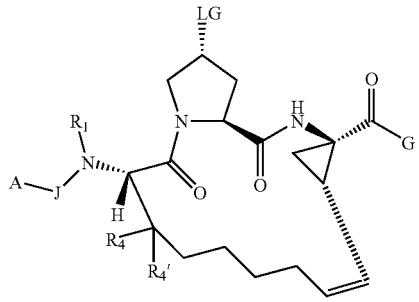

VI wherein:
LG is a leaving group;
T is

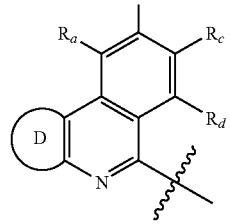

(for making Formula II) or

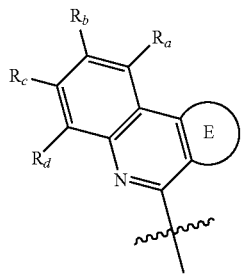

(for making Formula IV); and
A, J, G, $R_1$, $R_4$, $R_4'$, D. E, $R_a$, $R_b$, $R_c$, and $R_d$ are as described hereinabove.

The compounds of Formula I, II, III or IV can also be prepared according to the process depicted in Scheme 2, wherein A, J, G, T, $R_1$, $R_4$, and $R_4'$ are as described hereinabove, Q is halogen or a leaving group, PG and $PG_N$ are each independently an amino protecting group, $PG_C$ is a carboxylic acid protecting group; and wherein L' is $C_2$-$C_8$alkylene, $C_2$-$C_8$alkenylene or $C_2$-$C_8$alkynylene, each of which optionally contains 1 to 3 heteroatoms selected from O, S, S(O) or $S(O)_2$, and L' is optionally substituted with one or more substituents independently selected from halogen, hydroxy, mercapto, cyano, nitro, amino, carboxyl, formyl, $C_1$-$C_6$alkyl, $C_2$-$C_6$alkenyl or $C_2$-$C_6$alkynyl. Preferably, L' is (1) a $C_4$-$C_6$ saturated or unsaturated chain (alkylene, alkenylene or alkynylene) optionally containing one oxygen; (2) $C_2$-$C_8$alkylene, $C_2$-$C_8$alkenylene or $C_2$-$C_8$alkynylene, each of which optionally contains 1 to 3 heteroatoms selected from O, S, S(O) or $S(O)_2$; (3) $C_2$-$C_8$alkylene, $C_2$-$C_8$alkenylene or $C_2$-$C_8$alkynylene; or (4) or $C_{2-8}$ saturated or unsaturated chain, optionally containing one to three heteroatoms independently selected from O or S(O)m, wherein m is 0, 1 or 2. More preferably, L' is select from:

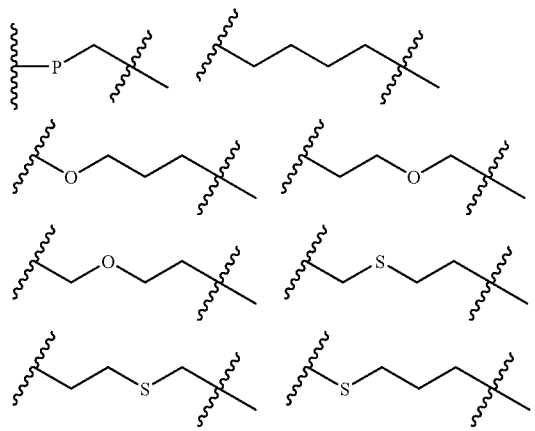

wherein P is as defined hereinabove. Highly preferably, L' is selected from:

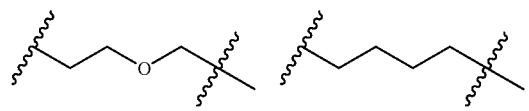

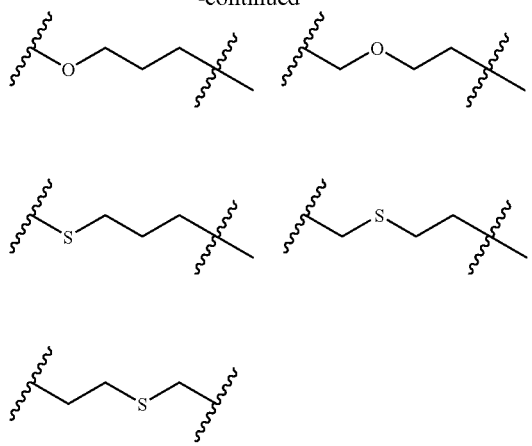

wherein P is as defined hereinabove.

Compound (b) in Scheme 2 can be prepared by reacting T-OH with a halogenation agent such as POCl$_3$. Non-limiting examples of amino protecting group include C$_1$-C$_6$alkoxycarbonyl (e.g., tert-butoxycarbonyl or Boc), carboxybenzyl, p-methoxybenzyl carbonyl, 9-fluorenylmethyloxycarbonyl, benzyl, p-methoxybenzyl, 3,4-dimethoxybenzyl, p-methoxyphenyl, benzoyl, or tosyl or other suitable sulfonamides. Non-limiting examples of carboxylic acid protecting group include C$_1$-C$_6$alkyl (e.g., tert-butyl, methyl or ethyl), benzyl, or silyl, all of which protect carboxylic acid moieties in the form of esters.

Scheme 2

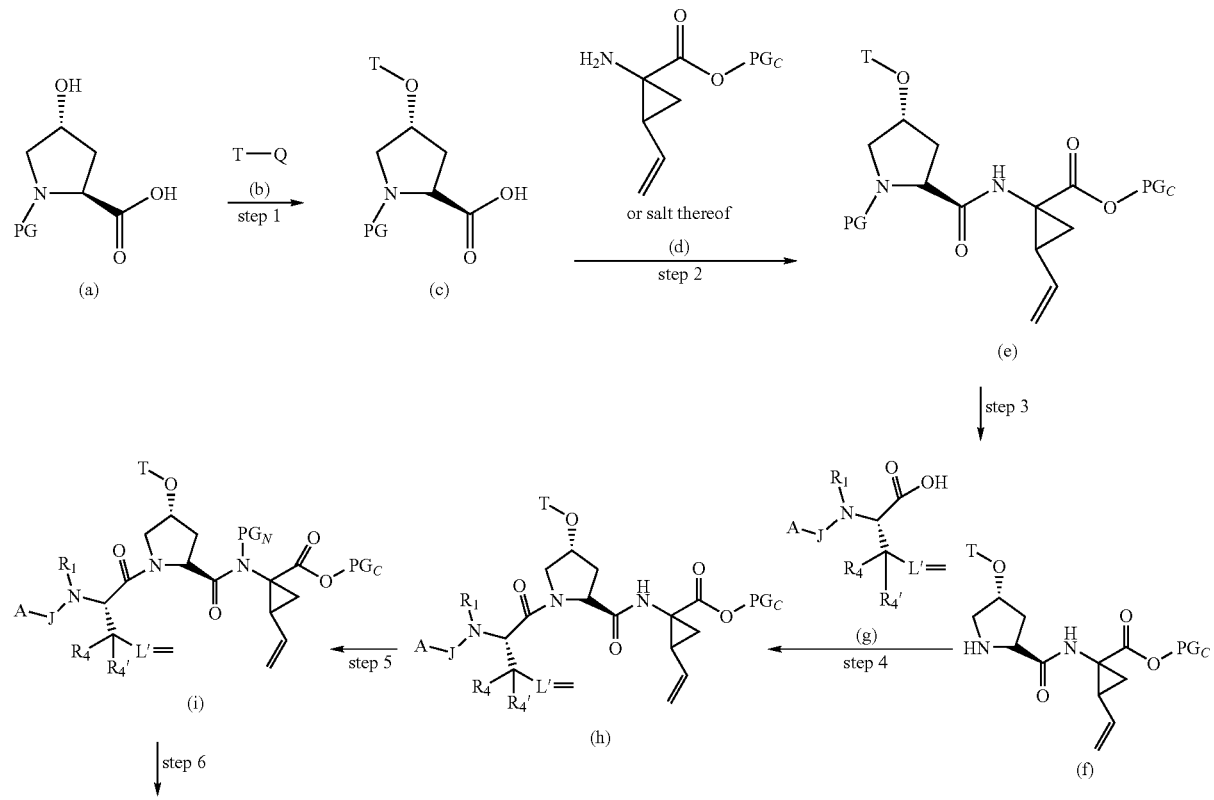

-continued

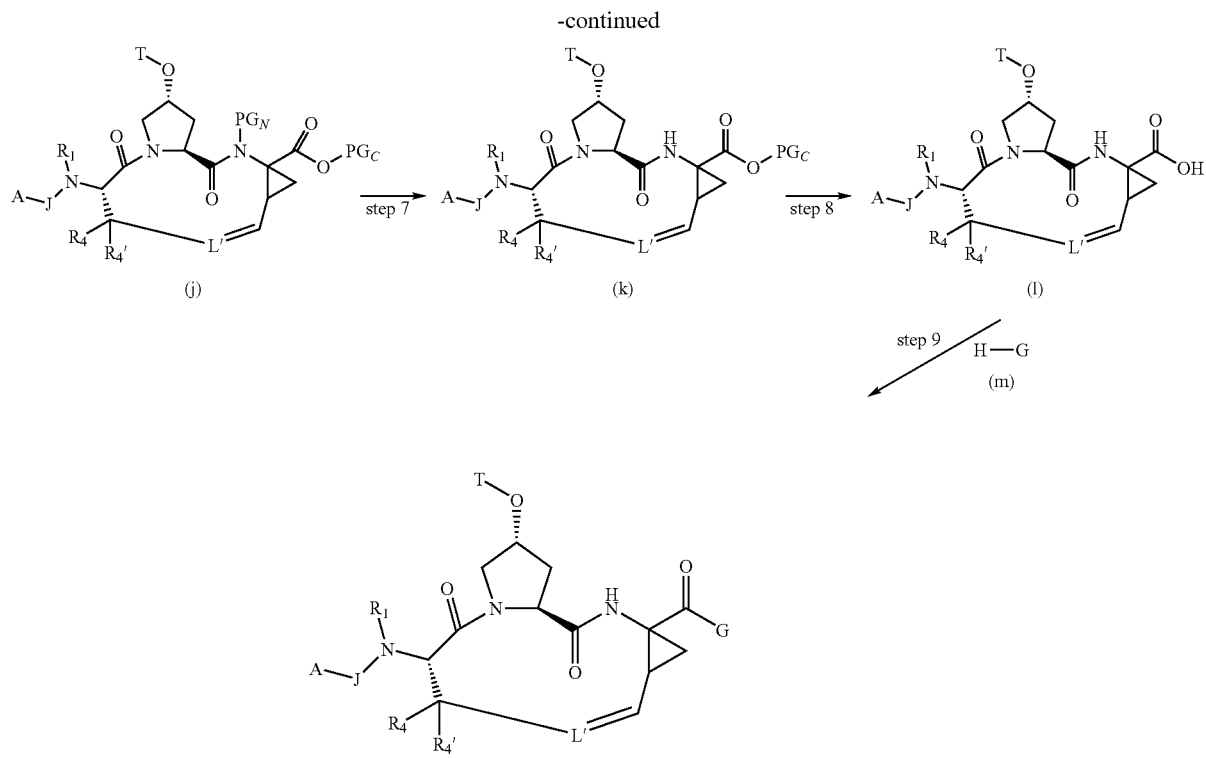

In step 1, compound (a) reacts with compound (b) to form compound (c), where the reaction can be conducted, as a non-limiting example, in the presence of sodium tert-butoxide or potassium tert-butoxide. Preferably, the reaction is conducted in the absence of lanthanum chloride. Also preferably, the yield of this reaction is at least 50%. More preferably, the yield of the reaction is at least 60%, 70%, or 80%. Highly preferably, the yield of the reaction is at least 90% or 95%. Preferred PG is $C_1$-$C_6$alkoxycarbonyl, such as tert-butoxycarbonyl or Boc.

Compound (c) can then be reacted with compound (d), or a salt thereof such as TsOH salt, to form compound (e) (step 2), followed by de-protection of the amino group to create compound (f) or a salt thereof (e.g., HCl salt) (step 3). Preferred $PG_C$ includes, but is not limited to, $C_1$-$C_6$alkyl such as ethyl. Compound (f) can then be reacted with compound (g) to form compound (h) (step 4), which is subsequently amino-protected to form compound (i) (step 5) and then subjected to ring-closing metathesis to form compound (j) (step 6). Preferred $PG_N$ includes, but is not limited to, $C_1$-$C_6$alkoxycarbonyl, such as tert-butoxycarbonyl or Boc. General processes for ring-closing metathesis (RCM) are well known in the art. Preferred processes involve the use of transition metal catalysts, such as those described in U.S. Pat. No. 6,921,753 and U.S. Patent Application Publication No. 20070043180. Non-limiting examples of suitable catalysts include Zhan Catalyst-1B

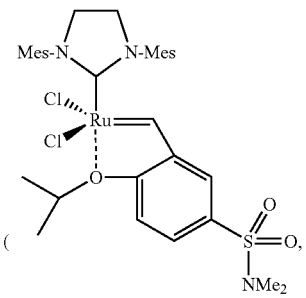

where Mes is 2,4,6-trimethylphenyl; also known as Zhan-B) and Zhan Catalyst-1C

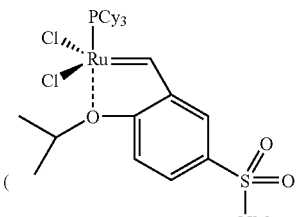

where Cy is cyclohexyl), both of which are commercially available from Zannan Pharma, Ltd. (Shanghai, China). De-protection of the amino moiety in compound (j) leads to compound (k) (or its free-base) (step 7). In certain cases, compound (h) can directly undergo the ring-closing metathesis reaction to make compound (k) (or its free-base), without the amino protecting and de-protecting steps.

The carboxylic acid moiety in compound (k) can then be deprotected to form compound (I) (step 8), which reacts with compound (m) to form compound (n) (step 9).

Likewise, a compound having the formula of

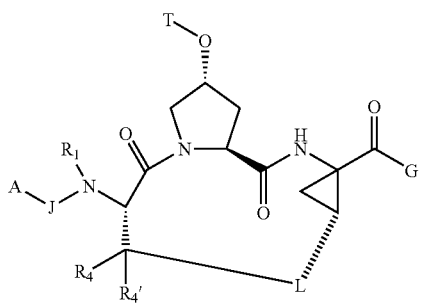

can be prepared by reacting a compound having the formula of

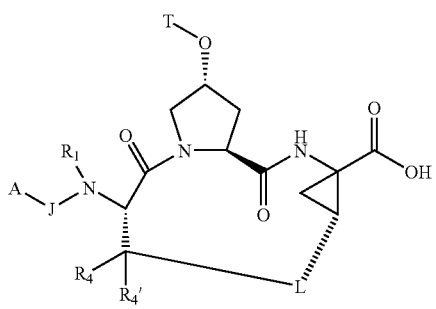

with G-OH, wherein A, J, $R_1$, $R_4$, $R_4'$, G, L, and T are as defined hereinabove.

The compounds of the invention can also be prepared using the processes described in U.S. Patent Application Publication No. 20070099825, which is incorporated herein in its entirety. This can be done by replacing R' and X (both of which are as defined in US Application Publication No. 20070099825) with T (as defined hereinabove) and O, respectively.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds and processes of the present invention will be better understood in connection with the following examples, which are intended as an illustration only and not to limit the scope of the invention. The following examples can be prepared according to Scheme 1, Scheme 2 or any other suitable methods. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

If a moiety described herein (e.g., —$NH_2$ or —OH) is not compatible with the synthetic methods, the moiety may be protected with a suitable protecting group that is stable to the reaction conditions used in the methods. The protecting group may be removed at a suitable point in the reaction sequence to provide a desired intermediate or target compound. Suitable protecting groups and methods for protecting or deprotecting moieties are well know in the art, examples of which can be found in Greene and Wuts, supra. Optimum reaction conditions and reaction times for each individual step may vary depending on the particular reactants employed and substituents present in the reactants used. Solvents, temperatures and other reaction conditions may be readily selected by one of ordinary skill in the art based on the present invention.

Other compounds of the invention can be similarly prepared according to the above-described schemes as well as the procedures described in following examples, as appreciated by those skilled in the art. It should be understood that the above-described embodiments and schemes and the following examples are given by way of illustration, not limitation. Various changes and modifications within the scope of the present invention will become apparent to those skilled in the art from the present description.

EXAMPLE 1 tert-butyl(2R,6S,13aS,14aR,16aS,Z)-14a-(cyclopropylsulfonylcarbamoyl)-5,16-dioxo-2-(7,8,9,10-tetrahydrophenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

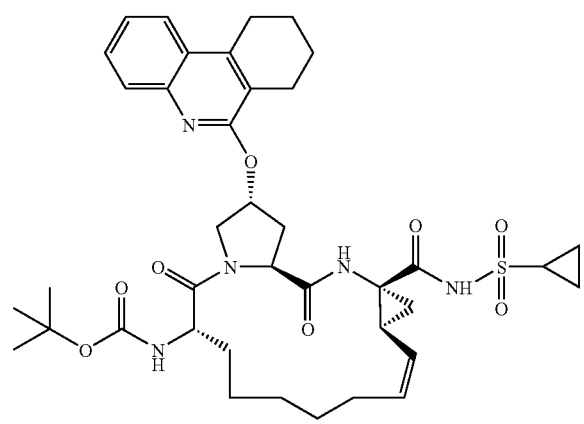

EXAMPLE 1a (2S,6S,13aS,14aR,16aS,Z)-ethyl 2-(4-bromophenyl-sulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

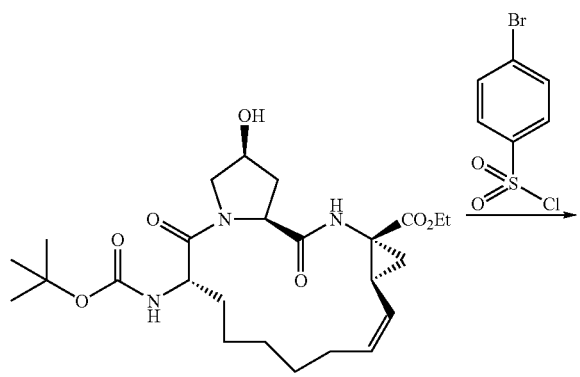

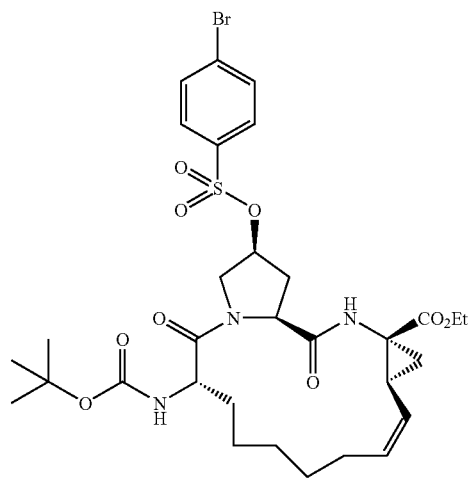

1a

A solution of (2S,6S,13aS,14aR,16aS,Z)-ethyl 6-(tert-butoxycarbonylamino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (22.1 g, 44.8 mmol) and DABCO (8.5 g, 76.7 mmol) in toluene (88 mL) may be stirred at room temperature. To this solution may be added a solution of 4-bromobenzene-1-sulfonyl chloride 17.2 g, 67.2 mmol) in toluene (44 mL). After the addition is complete the reaction mixture can be quenched with 10% aqueous sodium carbonate (110 mL) and the mixture stirred for 15 min. Tetrahydrofuran (44 mL) can be added and the mixture is washed with 0.5 M HCl, water, and then saturated aqueous sodium chloride. The organic layer may be dried over anhydrous magnesium sulfate, filtered, and evaporated under reduced pressure and dried to provide the title compound (27.7 g, 87% yield), which may be used without further purification.

EXAMPLE 1b

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 7,8,9,10-tetrahydrophenanthridin-6-ol (prepared according to the procedure of Bose, Ajay K., et al, *J. Heterocyclic Chem.* 1971, 8(6), 1091-1094) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 1c

To a solution of the product of Example 1b in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 1d

To a solution of product of Example 1c in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 2 tert-butyl(2R,6S,13aS,14aR,16aS,Z)-14a-(cyclopropylsulfonylcarbamoyl)-2-(2-methoxy-7,8,9,10-tetrahydrophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-

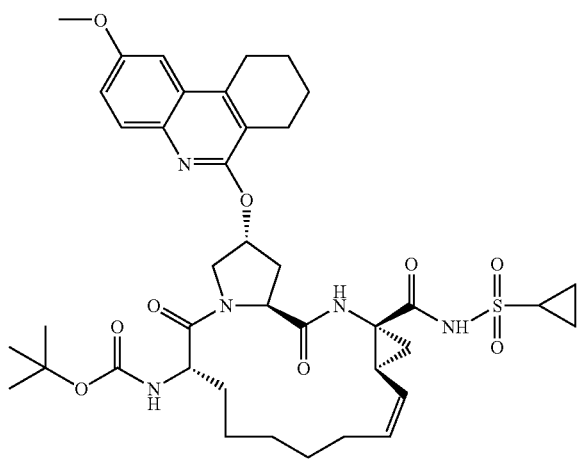

EXAMPLE 2a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 2-methoxy-7,8,9,10-tetrahydrophenanthridin-6-ol (prepared according to the procedure of Bose, Ajay K., et al, *J. Heterocyclic Chem.* 1971, 8(6), 1091-1094) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 2b

To a solution of the product of Example 2a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 2c

To a solution of product of Example 2b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 3 tert-butyl(2R,6S,13aS,14aR,16aS,Z)-14a-(cyclopropylsulfonylcarbamoyl)-2-(2,3-dihydro-1H-cyclopenta[c]quinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

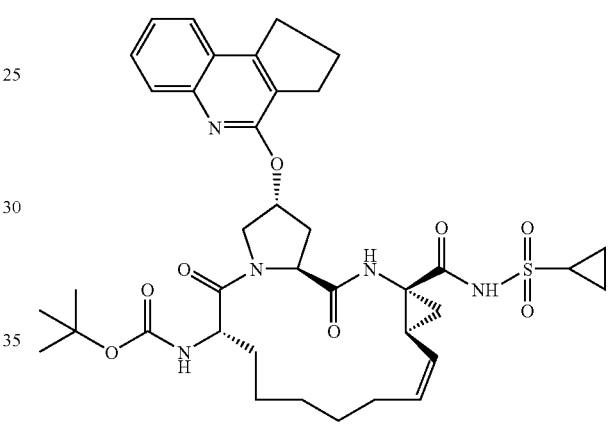

EXAMPLE 3a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 2,3-dihydro-1H-cyclopenta[c]quinolin-4-ol (prepared according to the procedure of Eisch, J. J. *J. Org. Chem.* 1978, 43, 2190-2196) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 3b

To a solution of the product of Example 3a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 3c

To a solution of product of Example 3b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 4 tert-butyl(2R,6S,13aS,14aR,16aS,Z)-14a-(cyclopropylsulfonylcarbamoyl)-2-(6-fluoro-2,3-dihydro-1H-cyclopenta[c]quinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

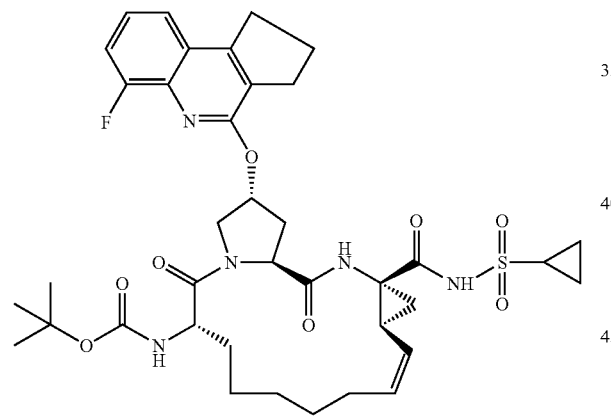

EXAMPLE 4a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 6-fluoro-2,3-dihydro-1H-cyclopenta[c]quinolin-4-ol (prepared according to the procedure of Jaroch, S., et al, Bioorganic & Medicinal Chemistry Letters 2004, 14, 743-746) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 4b

To a solution of the product of Example 4a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 4c

To a solution of product of Example 4b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 5 tert-butyl(2R,6S,13aS,14aR,16aS,Z)-14a-(cyclopropylsulfonylcarbamoyl)-2-(2,3-dihydrofuro[3,2-c]quinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

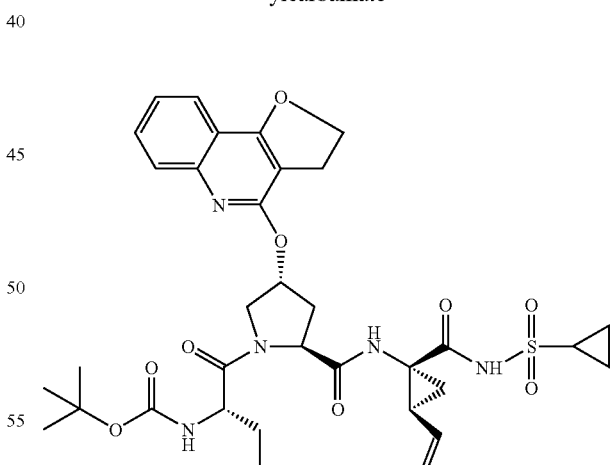

EXAMPLE 5a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 2,3-dihydrofuro[3,2-c]quinolin-4-ol (commercially available) followed by Cs₂CO₃. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 5b

To a solution of the product of Example 5a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous Na₂SO₄, and concentrated under reduced pressure to provide the title compound.

EXAMPLE 5c

To a solution of product of Example 5b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous Na₂SO₄, filtered, and concentrated under reduced pressure. The residue is purified by column chromatography on silica gel to obtain the title compound.

EXAMPLE 6 tert-butyl(2R,6S,13aS,14aR,16aS,Z)-14a-(cyclopropylsulfonylcarbamoyl)-5,16-dioxo-2-(1,2,3,4-tetrahydrophenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

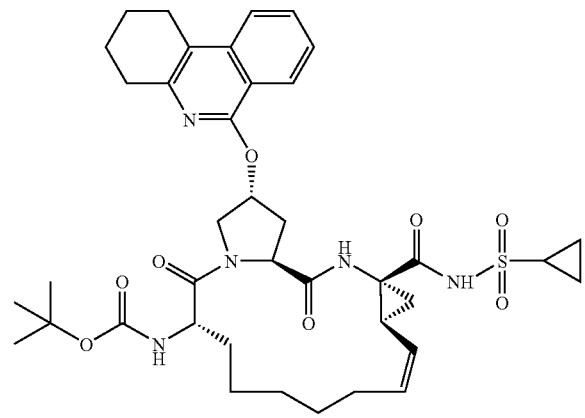

EXAMPLE 6a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 1,2,3,4-tetrahydrophenanthridin-6-ol (commercially available) followed by Cs₂CO₃. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 6b

To a solution of the product of Example 6a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous Na₂SO₄, and concentrated under reduced pressure to provide the title compound.

EXAMPLE 6c

To a solution of product of Example 6b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous Na₂SO₄, filtered, and concentrated under reduced pressure. The residue is purified by column chromatography on silica gel to obtain the title compound.

EXAMPLE 7 tert-butyl(2R,6S,13aS,14aR,16aS,Z)-14a-(cyclopropylsulfonylcarbamoyl)-2-(2,3-dihydro-1H-cyclopenta[c]isoquinolin-5-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

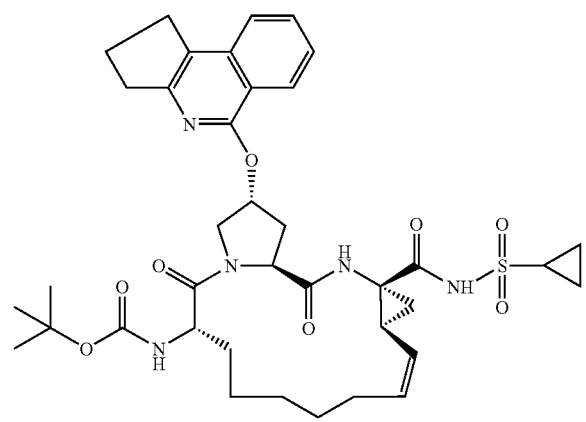

EXAMPLE 7a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 2,3-dihydro-1H-cyclopenta[c]isoquinolin-5-ol (prepared according to the method of Rigby, James, H. et al, *J. Org. Chem.* 1989, 54, 4019) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 7b

To a solution of the product of Example 7a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 7c

To a solution of product of Example 7b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 8

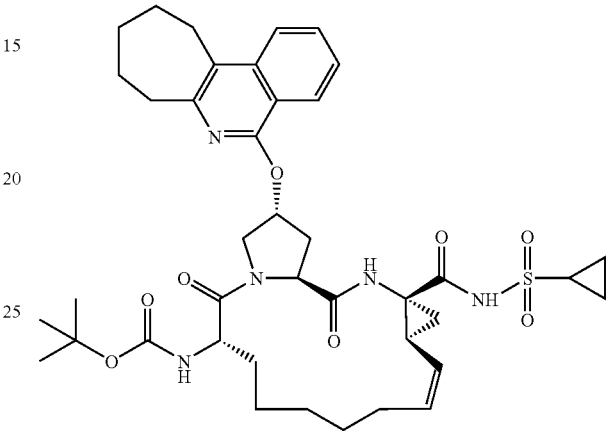

EXAMPLE 8a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 8,9,10,11-tetrahydro-7H-cyclohepta[c]isoquinolin-5-ol (prepared according to the method of Rigby, James, H. et al, *J. Org. Chem.* 1989, 54, 4019) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 8b

To a solution of the product of Example 8a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 8c

To a solution of product of Example 8b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 9 tert-butyl(2R,6S,13aS,14aR,16aS,Z)-2-(2-chloro-7,8, 9,10-tetrahydrophenanthridin-6-yloxy)-14a-(cyclopropylsulfonylcarbamoyl)-5,16-dioxo-1,2,3,5,6,7,8, 9,10,11,13a,14,14a,15,16,16a-hexadecahydrocyclopropa[e]pyrrolo[1,2-a][1,4]diazacyclopentadecin-6-ylcarbamate

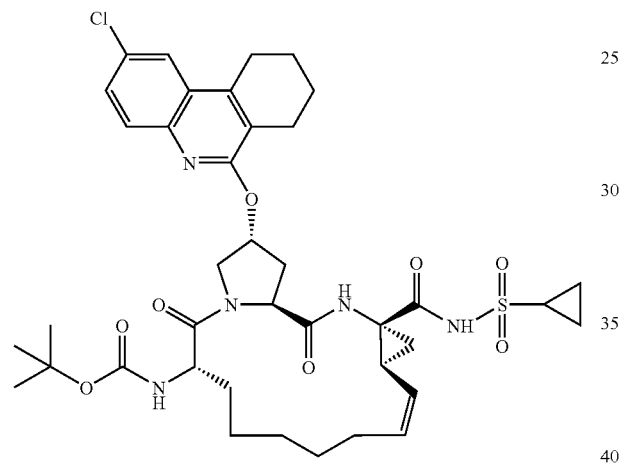

EXAMPLE 9a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in NMP (100 ml) is added 2-chloro-7,8,9,10-tetrahydrophenanthridin-6-ol (prepared according to the method of Bose, Ajay K., et al, *J. Heterocyclic Chem.* 1971, 8(6), 1091-1094) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 9b

To a solution of the product of Example 9a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 9c

To a solution of product of Example 9b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 10 tert-butyl(2R,6S,13aS,14aR,16aS,Z)-14a-(cyclopropylsulfonylcarbamoyl)-2-(8-methoxy-2,3-1H-cyclopenta[c]quinolin-4-yloxy)-5,16-dioxo-1,2,3,5,6,7,8, 9,10,11,13a,14,14a,15,16,16a-hexadecahydrocyclopropa[e]pyrrolo[1,2-a][1,4]diazacyclopentadecin-6-ylcarbamate

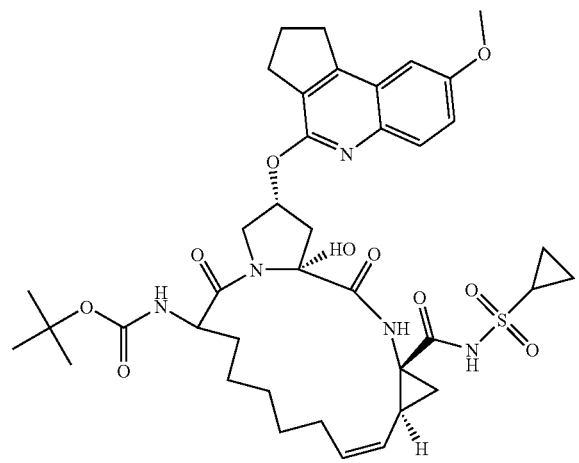

EXAMPLE 10a

To a solution of compound (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15, 16,16a-hexadecahydrocyclopropa[e]pyrrolo[1,2-a][1,4]diazacyclopentadecine-14a-carboxylate in NMP (100 ml) is added 8-methoxy-2,3-dihydro-1H-cyclopenta[c]quinolin-4-ol (prepared according to the method of Ried, W., Kaeppeler, W., *J. Liebigs Analen der Chemie,* 1965, 688, 177-188) followed by $Cs_2CO_3$. The resulting mixture is heated to 55° C. for four hours. The reaction mixture is cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. The solid is then purified by crystallization or column chromatography to provide the title compound.

EXAMPLE 10b

To a solution of the product of Example 10a in tetrahydrofuran/ethanol is added an aqueous lithium hydroxide solution. The resulting mixture is heated to 50° C. for two hours and cooled to room temperature. The organic solvents is mostly removed under reduced pressure, and the resulting residue is acidified with 10% citric acid aqueous solution and extracted with ethyl acetate. The organic layer is separated, washed with brine (200 ml), dried over anhydrous $Na_2SO_4$, and concentrated under reduced pressure to provide the title compound.

EXAMPLE 10c

To a solution of product of Example 10b in DMF is added 1,1'-carbomyldiimidazole. The reaction mixture is stirred at room temperature for 6 hours. To the above solution is added cyclopropanesulfonamide followed by DBU. The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride (100 ml), dried over anhydrous $Na_2SO_4$, filtered, and concentrated under reduced pressure. The residue is purified by column chromatography on silica gel to obtain the title compound.

EXAMPLE 11 tert-butyl(2R,6S,13aS,14aR,16aS,Z)-2-(benzo[c][1,8]naphthyridin-6-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

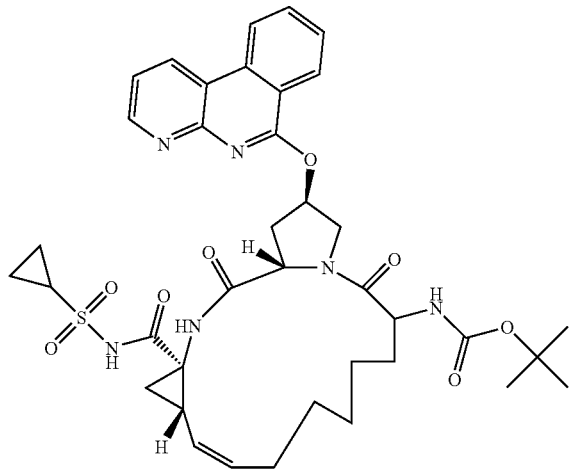

EXAMPLE 11a (2R,6S,13aS,14aR,16aS,Z)-ethyl 2-(benzo[c][1,8]naphthyridin-6-yloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate To a solution of compound 1a in DMSO is added benzo[c][1,8]naphthyridin-6-ol (78a, 1.5 eq, prepared as described by D. Ferraris et al, *J. Med. Chem.* 2003, 46(14), 3138-3151) followed by $Cs_2CO_3$ (1.5 eq). The resulting mixture is heated to 65° C., cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. This material is purified by chromatography or by recrystallization.

EXAMPLE 11b (2R,6S,13aS,14aR,16aS,Z)-2-(benzo[c][1,8]naphthyridin-6-yloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid To a solution of the product of Example 1a in tetrahydrofuran/ethanol is added an aqueous lithium hydroxide solution. The resulting mixture is heated to 50° C. and then cooled to room temperature. The organic solvents are concentrated under reduced pressure, and the resulting residue is acidified with 10% citric acid aqueous solution and extracted with ethyl acetate. The organic layer is separated, washed with brine, dried over anhydrous $Na_2SO_4$, and concentrated under reduced pressure to provide the title compound.

EXAMPLE 11c

To a solution of the product of Example 11b in DMF is added 1,1'-carbomyldiimidazole (3 eq). The reaction mixture is stirred at room temperature for 6 hours. To the above solution is then added the cyclopropanesulfonamide (3 eq) followed by DBU (3.1 eq). The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride, dried over anhydrous $Na_2SO_4$, filtered, and concentrated under reduced pressure. The residue is purified by column chromatography on silica gel to obtain the title compound.

EXAMPLE 12

(2R,6S,13aS,14aR,16aS,Z)-2-(benzo[c][1,8]naphthy-ridin-6-yloxy)-N-(cyclopropylsulfonyl)-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

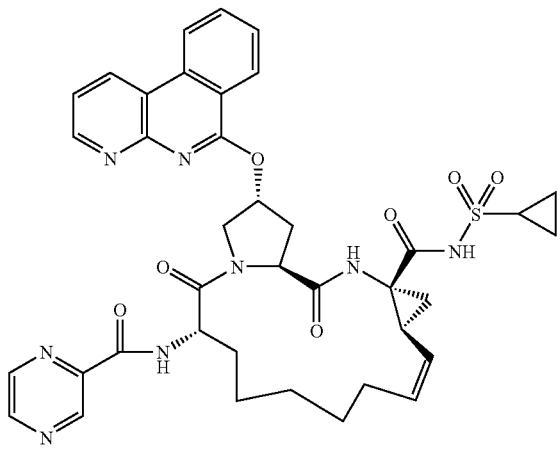

EXAMPLE 12a (2R,6S,13aS,14aR,16aS,Z)-6-amino-2-(benzo[c][1,8]naphthyridin-6-yloxy)-N-(cyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride To a suspension of the product of Example 11 in acetonitrile is added a 4 M solution of HCl in dioxane. The reaction mixture is stirred at rt for 4 h. The solvent is evaporated under reduced pressure and the resulting solid dried under vacuum to provide the title compound 79a.

EXAMPLE 12b

To a solution of Example 12a in dimethylformamide is added pyrazinecarboxylic acid (1.1 eq), HATU (1.2 eq) and diisopropylethylamine (2.5 eq). The reaction mixture is stirred at 25° C. until complete then is partitioned between 5% aqueous sodium bicarbonate and ethyl acetate. The organic layer is dried over anhydrous magnesium sulfate, filtered, and evaporated. The residue is purified by chromatography or recrystallization to provide the title compound 79.

EXAMPLE 13

(2R,6S,13aS,14aR,16aS,Z)-2-(benzo[c][1,8]naphthyridin-6-yloxy)-N-(cyclopropylsulfonyl)-6-(5-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide

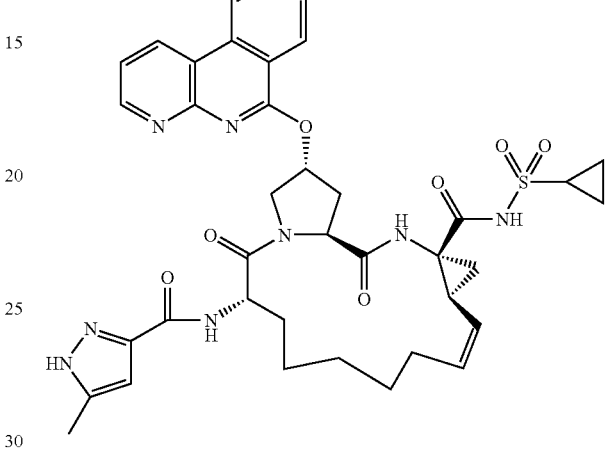

Example 13 is prepared according to the procedure utilized for the preparation of Example 12, replacing 2-pyrazinecarboxylic acid with 5-methyl-1H-pyrazole-3-carboxylic acid.

EXAMPLE 14

N-((2R,6S,13aS,14aR,16aS,Z)-2-(benzo[c][1,8]naphthyridin-6-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide

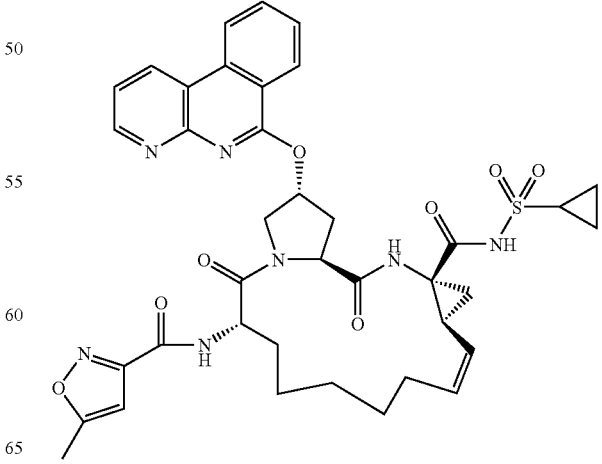

Example 14 is prepared according to the procedure utilized for the preparation of Example 12, replacing 2-pyrazinecarboxylic acid with 5-methylisoxazole-3-carboxylic acid.

EXAMPLE 15

(2R,6S,13aS,14aR,16aS,Z)-2-(benzo[c][1,8]naphthyridin-6-yloxy)-N-(cyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide

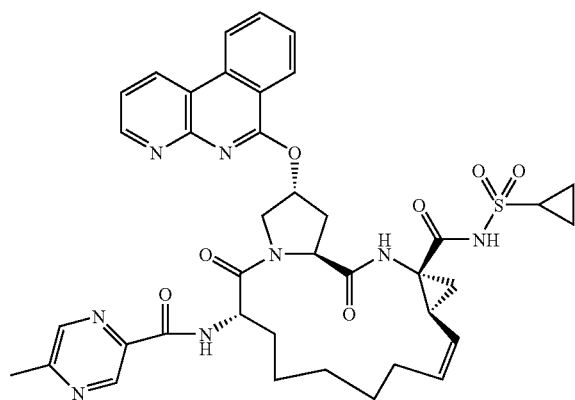

Example 15 is prepared according to the procedure utilized for the preparation of Example 12, replacing 2-pyrazinecarboxylic acid with 5-methylpyrazine-2-carboxylic acid.

EXAMPLE 16

N-((2R,6S,13aS,14aR,16aS,Z)-2-(benzo[c][1,8]naphthyridin-6-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-5-carboxamide

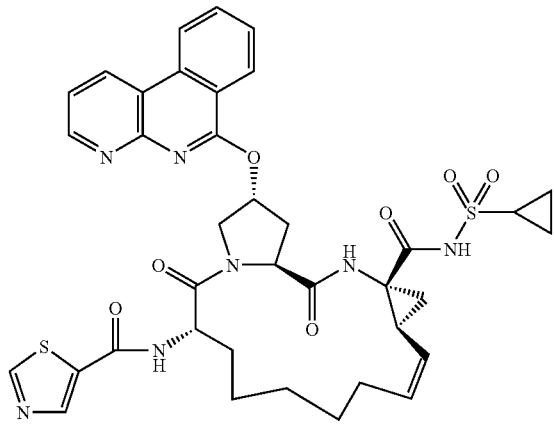

Example 16 is prepared according to the procedure utilized for the preparation of Example 12, replacing 2-pyrazinecarboxylic acid with thiazole-5-carboxylic acid.

EXAMPLE 17

(2R,6S,13aS,14aR,16aS,Z)-2-(benzo[c][1,8]naphthyridin-6-yloxy)-N-(cyclopropylsulfonyl)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide

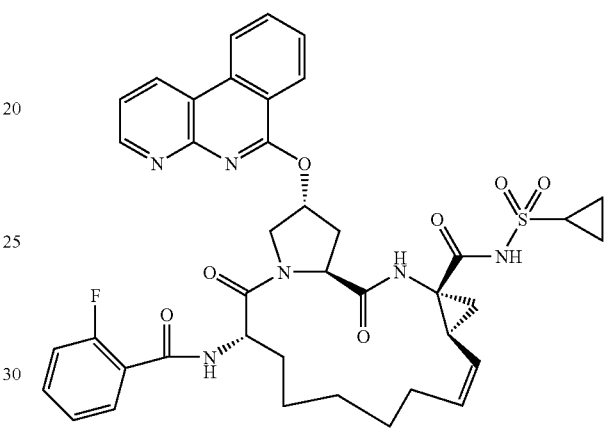

Example 17 is prepared according to the procedure utilized for the preparation of Example 12, replacing 2-pyrazinecarboxylic acid with 2-fluorobenzoic acid.

EXAMPLE 18

(2R,6S,13aS,14aR,16aS,Z)-2-(benzo[c][1,8]naphthyridin-6-yloxy)-N-(cyclopropylsulfonyl)-5,16-dioxo-6-(pyridazine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

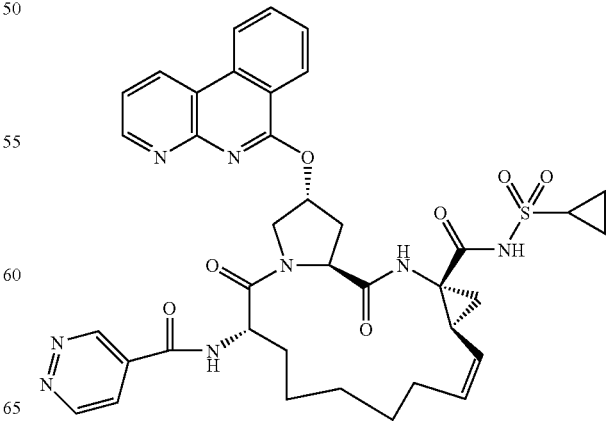

Example 18 is prepared according to the procedure utilized for the preparation of Example 12, replacing 2-pyrazinecarboxylic acid with pyridazine-4-carboxylic acid.

EXAMPLE 19

(2R,6S,13aS,14aR,16aS,Z)-2-(benzo[c][1,8]naphthyridin-6-yloxy)-N-(cyclopropylsulfonyl)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

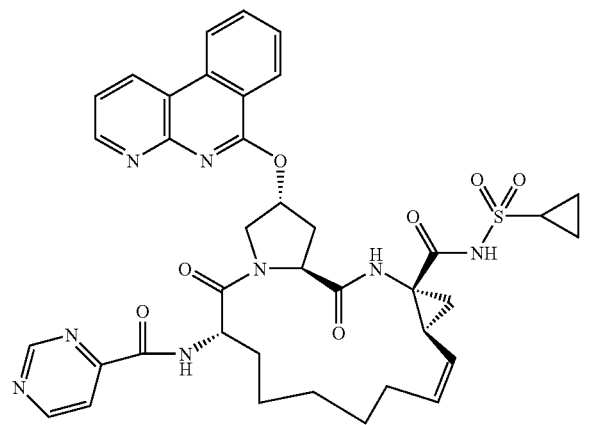

Example 19 is prepared according to the procedure utilized for the preparation of Example 12, replacing 2-pyrazinecarboxylic acid with pyrimidine-4-carboxylic acid.

EXAMPLE 20

(2R,6S,13aS,14aR,16aS,Z)-2-(benzo[c][1,8]naphthyridin-6-yloxy)-N-(cyclopropylsulfyl)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide

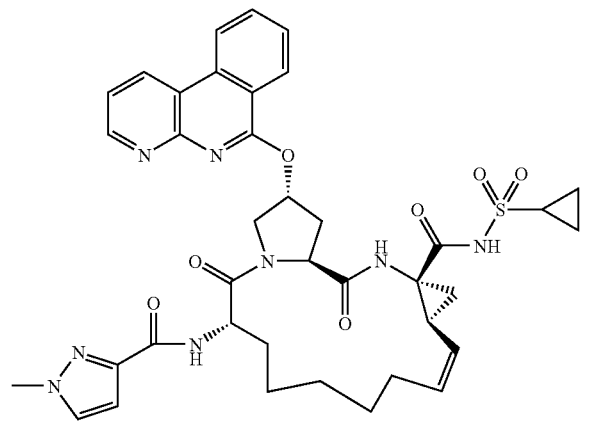

Example 20 is prepared according to the procedure utilized for the preparation of Example 12, replacing 2-pyrazinecarboxylic acid with 1-methyl-1H-pyrazole-3-carboxylic acid.

EXAMPLE 21

(2R,6S,13aS,14aR,16aS,Z)-2-(benzo[c][1,8]naphthyridin-6-yloxy)-N-(cyclopropylsulfonyl)-6-(1,5-dimethyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide

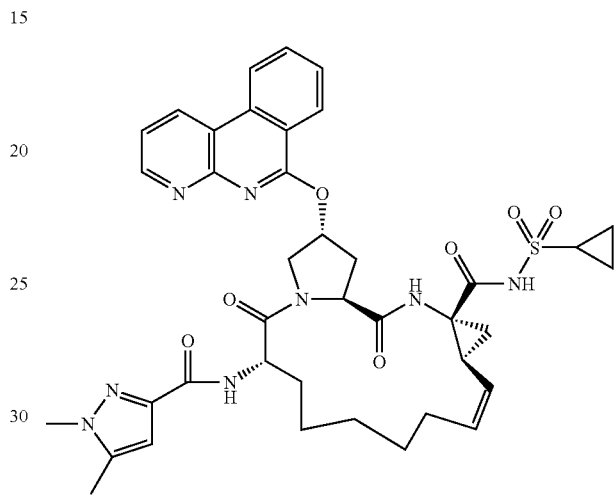

Example 21 is prepared according to the procedure utilized for the preparation of Example 12, replacing 2-pyrazinecarboxylic acid with 1,5-dimethyl-1H-pyrazole-3-carboxylic acid.

EXAMPLE 22 tert-butyl (2R,6S,13aS,14aR,16aS,Z)-14a-(cyclopropylsulfonylcarbamoyl)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

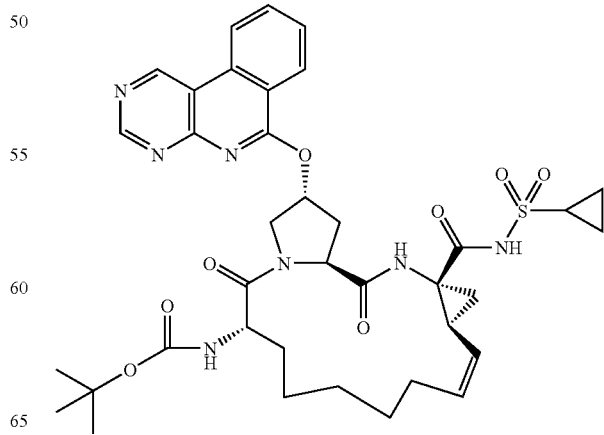

EXAMPLE 22a (2R,6S,13aS,14aR,16aS,Z)-ethyl 2-(benzo [c][1,8] naphthyridin-6-yloxy)-6-(tert-butoxycarbonylamino)-5,16-dioxo-1,2,3,5,6,7,8,9,10,11,13a,14,14a, 15,16,16a-hexadecahydrocyclopropa[e]pyrrolo[1,2-a][1,4]diazacyclopentadecine-14a-carboxylate To a solution of compound la in DMSO is added pyrimido[4,5-c]isoquinolin-6-ol (89a, 1.5 eq, prepared as described by A. Rosowsky et al, *J. Het. Chem.* 1974, 11(6), 1081-1084) followed by Cs$_2$CO$_3$ (1.5 eq). The resulting mixture is heated to 65° C., cooled to room temperature, and then partitioned between ethyl acetate and 5% aqueous sodium bicarbonate solution. The organic layer is separated, washed with 5% aqueous sodium bicarbonate solution followed by brine, dried over anhydrous sodium sulfate, and concentrated under reduced pressure to obtain the crude product. This material is purified by chromatography or by recrystallization.

EXAMPLE 22b (2R,6S,13aS,14aR,16aS,Z)-6-(tert-butoxycarbonylamino)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid To a solution of the product of Example 22a in tetrahydrofuran/ethanol is added an aqueous lithium hydroxide solution. The resulting mixture is heated to 50° C. and then cooled to room temperature. The organic solvents are concentrated under reduced pressure, and the resulting residue is acidified with 10% citric acid aqueous solution and extracted with ethyl acetate. The organic layer is separated, washed with brine, dried over anhydrous Na$_2$SO$_4$, and concentrated under reduced pressure to provide the title compound.

EXAMPLE 22c

To a solution of the product of Example 22b in DMF is added 1,1'-carbomyldiimidazole (3 eq). The reaction mixture is stirred at room temperature for 6 hours. To the above solution is then added the cyclopropanesulfonamide (3 eq) followed by DBU (3.1 eq). The resulting mixture is stirred at room temperature for 14 hours. To the reaction mixture is added EtOAc, 10% aqueous citric acid solution, and saturated anhydrous sodium chloride. The organic layer is separated, washed with saturated anhydrous sodium chloride, dried over anhydrous Na$_2$SO$_4$, filtered, and concentrated under reduced pressure. The residue is purified by column chromatography on silica gel to obtain the title compound.

EXAMPLE 23

(2R,6S,13aS,14aR,16aS,Z)-N-(cyclopropylsulfonyl)-5,16-dioxo-6-(pyrazine-2-carboxamido)-2-(pyrimido[4,5-c]isoquinolin-6-yloxy)-1,2,3,5,6,7,8,9,10,11, 13a,14,14a,15,16,16a-hexadecahydrocyclopropa[e]pyrrolo[1,2-a][1,4]diazacyclopentadecine-14a-carboxamide

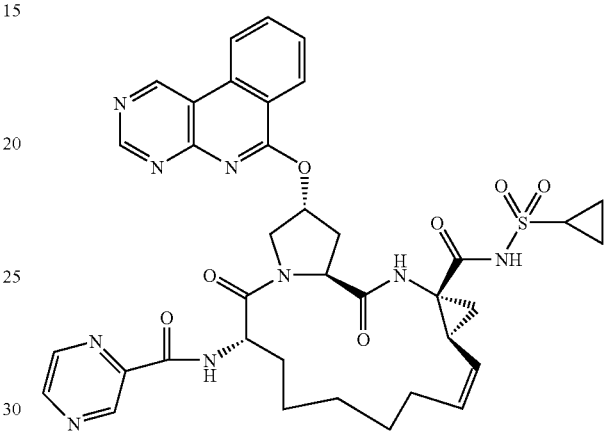

EXAMPLE 23a (2R,6S,13aS,14aR,16aS,Z)-6-amino-N-(cyclopropylsulfonyl)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride To a suspension of the product of Example 22 in acetonitrile is added a 4 M solution of HCl in dioxane. The reaction mixture is stirred at rt for 4 h. The solvent is evaporated under reduced pressure and the resulting solid dried under vacuum to provide the title compound 90a.

EXAMPLE 23b

To a solution of Example 23a in dimethylformamide is added pyrazinecarboxylic acid (1.1 eq), HATU (1.2 eq) and diisopropylethylamine (2.5 eq). The reaction mixture is stirred at 25° C. until complete then is partitioned between 5% aqueous sodium bicarbonate and ethyl acetate. The organic layer is dried over anhydrous magnesium sulfate, filtered, and evaporated. The residue is purified by chromatography or recrystallization to provide the title compound 90.

EXAMPLE 24

(2R,6S,13aS,14aR,16aS,Z)-N-(cyclopropylsulfonyl)-6-(5-methyl-1H-pyrazole-3-carboxamido)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

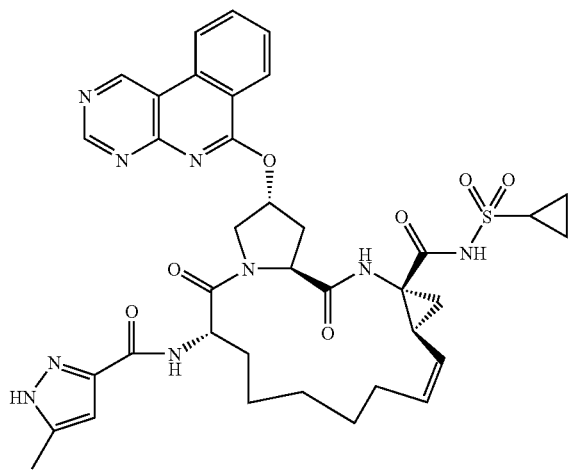

Example 24 is prepared according to the procedure utilized for the preparation of Example 23, replacing 2-pyrazinecarboxylic acid with 5-methyl-1H-pyrazole-3-carboxylic acid.

EXAMPLE 25

N-((2R,6S,13aS,14aR,16aS,Z)-14a-(cyclopropylsulfonylcarbamoyl)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide

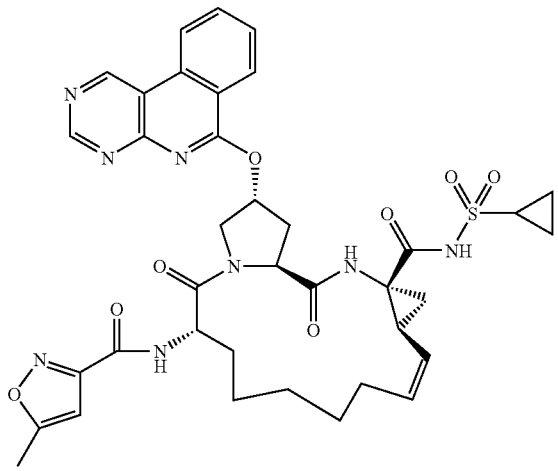

Example 25 is prepared according to the procedure utilized for the preparation of Example 23, replacing 2-pyrazinecarboxylic acid with 5-methylisoxazole-3-carboxylic acid.

EXAMPLE 26

(2R,6S,13aS,14aR,16aS,Z)-N-(cyclopropylsulfonyl)-6-(5-methylpyrazine-2-carboxamido)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

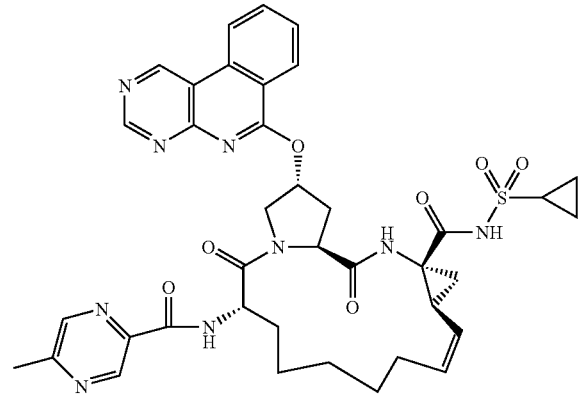

Example 26 is prepared according to the procedure utilized for the preparation of Example 23, replacing 2-pyrazinecarboxylic acid with 5-methylpyrazine-2-carboxylic acid.

EXAMPLE 27

N-((2R,6S,13aS,14aR,16aS,Z)-14a-(cyclopropylsulfonylcarbamoyl)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-5-carboxamide

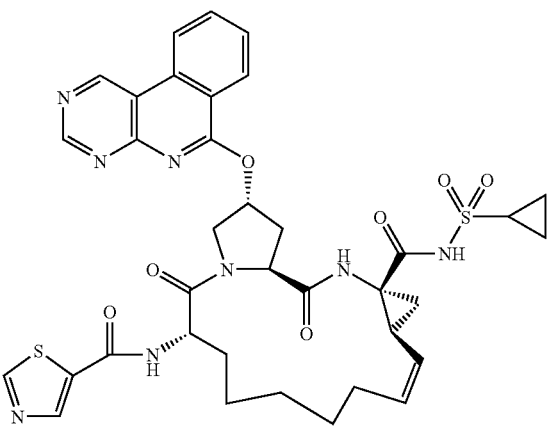

Example 27 is prepared according to the procedure utilized for the preparation of Example 23, replacing 2-pyrazinecarboxylic acid with thiazole-5-carboxylic acid.

EXAMPLE 28

(2R,6S,13aS,14aR,16aS,Z)-N-(cyclopropylsulfonyl)-6-(2-fluorobenzamido)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

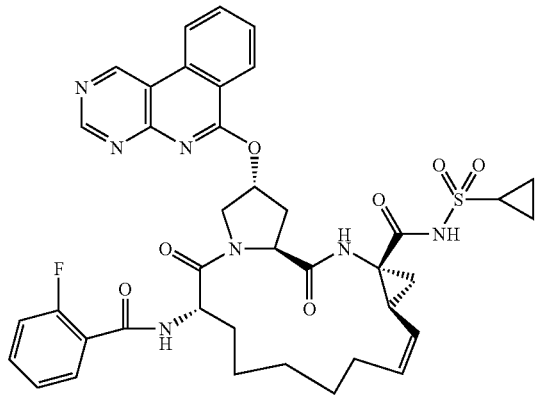

Example 28 is prepared according to the procedure utilized for the preparation of Example 23, replacing 2-pyrazinecarboxylic acid with 2-fluorobenzoic acid.

EXAMPLE 29

(2R,6S,13aS,14aR,16aS,Z)-N-(cyclopropylsulfonyl)-5,16-dioxo-6-(pyridazine-4-carboxamido)-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

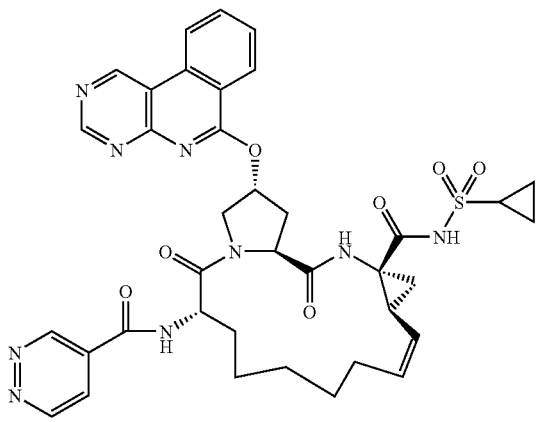

Example 29 is prepared according to the procedure utilized for the preparation of Example 23, replacing 2-pyrazinecarboxylic acid with pyridazine-4-carboxylic acid.

EXAMPLE 30

(2R,6S,13aS,14aR,16aS,Z)-N-(cyclopropylsulfonyl)-5,16-dioxo-6-(pyrimidine-4-carboxamido)-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

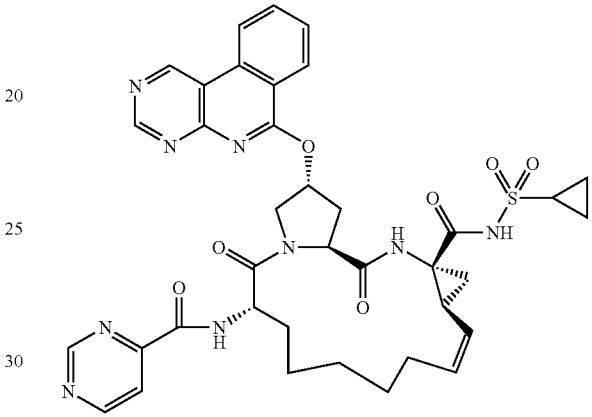

Example 30 is prepared according to the procedure utilized for the preparation of Example 23, replacing 2-pyrazinecarboxylic acid with pyrimidine-4-carboxylic acid.

EXAMPLE 31

(2R,6S,13aS,14aR,16aS,Z)-N-(cyclopropylsulfonyl)-6-(1-methyl-1H-pyrazole-3-carboxamido)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

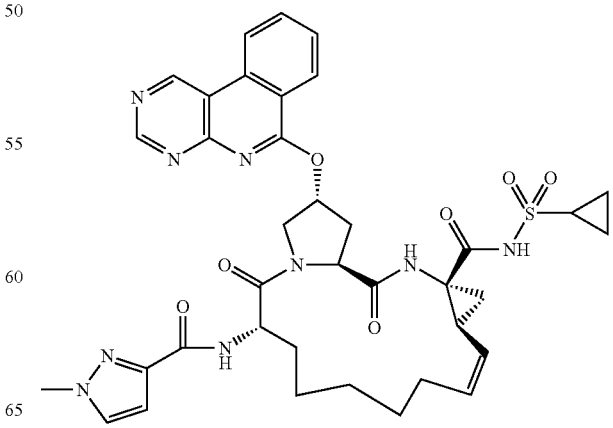

Example 31 is prepared according to the procedure utilized for the preparation of Example 23, replacing 2-pyrazinecarboxylic acid with 1-methyl-1H-pyrazole-3-carboxylic acid.

EXAMPLE 32

(2R,6S,13aS,14aR,16aS,Z)-N-(cyclopropylsulfonyl)-6-(1,5-dimethyl-1H-pyrazole-3-carboxamido)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

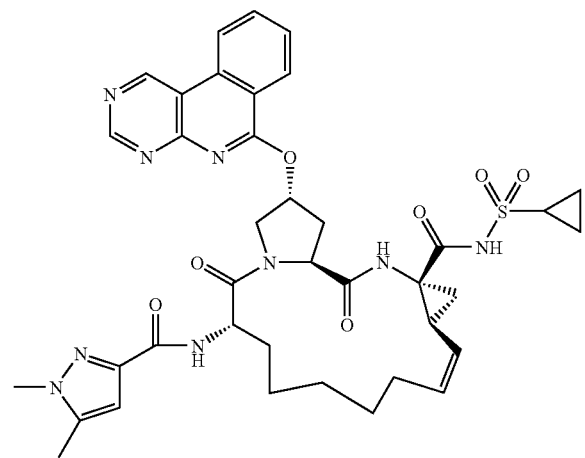

Example 32 is prepared according to the procedure utilized for the preparation of Example 23, replacing 2-pyrazinecarboxylic acid with 1,5-dimethyl-1H-pyrazole-3-carboxylic acid.

EXAMPLE 33

Measurement of Potency of Inhibition with Purified NS3 Protease Enzyme

The activity of recombinant HCV NS3 proteases derived from isolates representing genotypes 1, 2, 3 or 4 may be measured by cleavage of the following peptide substrate:

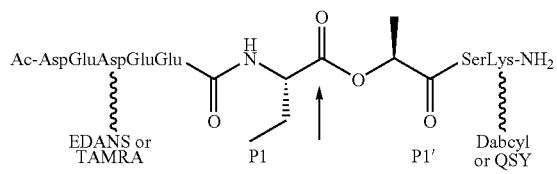

The substrate may be labeled with a fluor and a fluorescence quencher. Cleavage results in release of the quencher and an increase in fluorescence. NS3 protease is incubated with a dilution series of inhibitor in 150 mM NaCl, 10% Glycerol, 5 mM DTT, with or without 0.01% dodecyl maltoside for either 30 minutes or 300 minutes. Substrate is added at a concentration of 5 uM to initiate the reaction, and fluorescence is measured at 2 minute intervals for 30 minutes. Enzyme concentrations range from 10 to 100 nM in the absence of detergent, or 10-fold lower in the presence of detergent. Substrate peptides are labeled with either EDANS and DABCYL (excitation 355 nm, emission 485 nm) or TAMRA and QSY (excitation 544 nm, emission 590 nm). For routine IC50 determination, 3-fold serial dilutions starting with initial concentrations of 100 μM, 200 μM, or 2 mM are used. For compounds with $K_i$ values approaching or lower than the enzyme concentration, a tight-binding calculation format is used, with 24 dilutions of inhibitor covering a range of 0 to 100 nM inhibitor. $K_i$ values are calculated using the tight binding assay format, according to the following equation:

$V=A\{[(K+I-E)^2+4KE])^{1/2}-(K+I-E)\}$, where $I$=total inhibitor concentration, $E$=active enzyme concentration, $K$=apparent $K_i$ value and $A=[k_{cat}]S/2]$ [$K_m=(S)$].

Replicon Cell Lines

The inhibitory activities of the compounds of the present invention can be evaluated using Replicon cell lines. For instance, two stable subgenomic replicon cell lines can be used for compound characterization in cell culture: one derived from genotype 1a-H77 and the other derived from genotype 1b-Con1 (obtained from Apath, LLC, St. Louis, Mo.). The replicon constructs can be bicistronic subgenomic replicons. The genotype 1a replicon construct contains NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 replicon construct is identical to the 1a-H77 replicon, except that the NS3-NS5B coding region is derived from the 1b-Con1 strain, and the adaptive mutations are E1202G, T1280I and S2204I. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can be determined by measuring activity of the luciferase reporter gene. For example, replicon-containing cells can be seeded into 96 well plates at a density of 5000 cells per well in 100 μl DMEM containing 5% FBS. The following day compounds can be diluted in dimethyl sulfoxide (DMSO) to generate a 200× stock in a series of eight half-log dilutions. The dilution series can then be further diluted 100-fold in the medium containing 5% FBS. Medium with the inhibitor is added to the overnight cell culture plates already containing 100 μl of DMEM with 5% FBS. In assays measuring inhibitory activity in the presence of human plasma, the medium from the overnight cell culture plates can be replaced with DMEM containing 40% human plasma and 5% FBS. The cells can be incubated for three days in the tissue culture incubators and are then lysed for RNA extraction. For the luciferase assay, 30 μl of Passive Lysis buffer (Promega) can be added to each well, and then the plates are incubated for 15 minutes with rocking to lyse the cells. Luciferin solution (100 μl, Promega) can be added to each well, and luciferase activity can be measured with a Victor II luminometer (Perkin-Elmer). The percent inhibition of HCV RNA replication can be calculated for each compound concentration and the $IC_{50}$ and/or $EC_{50}$ value can be calculated sing nonliniear regression curve fitting to the 4-parameter logistic equation and GraphPad Prism 4 software Using the above-described assays or similar cell-based replicon arrays, representative compounds of the present invention can be shown to have significant inhibitory activities against the replication of HCV, including HCV mutants.

The present invention also features pharmaceutical compositions comprising the compounds of the invention. A pharmaceutical composition of the present invention can comprise one or more compounds of the invention, each of which has Formula I, II, III, or IV.

In addition, the present invention features pharmaceutical compositions comprising pharmaceutically acceptable salts of the compounds of the invention. Without limitation, pharmaceutically acceptable salts can be zwitterions or derived from pharmaceutically acceptable inorganic or organic acids or bases. Preferably, a pharmaceutically acceptable salt retains the biological effectiveness of the free acid or base of the compound without undue toxicity, irritation, or allergic response, has a reasonable benefit/risk ratio, is effective for the intended use, and is not biologically or otherwise undesirable.

The present invention further features pharmaceutical compositions comprising a compound of the invention (or a salt thereof) and another therapeutic agent. By way of illustration not limitation, these other therapeutic agents can be selected from antiviral agents (e.g., anti-HIV agents, anti-HBV agents, or other anti-HCV agents such as HCV protease inhibitors, HCV polymerase inhibitors, HCV helicase inhibitors, IRES inhibitors or NS5A inhibitors), anti-bacterial agents, anti-fungal agents, immunomodulators, anti-cancer or chemotherapeutic agents, anti-inflammation agents, antisense RNA, siRNA, antibodies, or agents for treating cirrhosis or inflammation of the liver. Specific examples of these other therapeutic agents include, but are not limited to, ribavirin, α-interferon, β-interferon, pegylated interferon-α, pegylated interferon-lambda, ribavirin, viramidine, R-5158, nitazoxanide, amantadine, Debio-025, NIM-811, R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728, GL60667, BMS-790052, BMS-791325, BMS-650032, GS-9132, ACH-1095, AP-H005, A-831, A-689, AZD2836, telaprevir, boceprevir, ITMN-191, BI-201335, VBY-376, VX-500 (Vertex), PHX-B, ACH-1625, IDX136, IDX316, VX-813 (Vertex), SCH 900518 (Schering-Plough), TMC-435 (Tibotec), ITMN-191 (Intermune, Roche), MK-7009 (Merck), IDX-PI (Novartis), BI-201335 (Boehringer Ingelheim), R7128 (Roche), PSI-7851 (Pharmasset), MK-3281 (Merck), PF-868554 (Pfizer), IDX-184 (Novartis), IDX-375 (Pharmasset), BILB-1941 (Boehringer Ingelheim), GS-9190 (Gilead), BMS-790052 (BMS), Albuferon (Novartis), ritonavir, another cytochrome P450 monooxygenase inhibitor, or any combination thereof.

In one embodiment, a pharmaceutical composition of the present invention comprises one or more compounds of the present invention (or salts thereof), and one or more other antiviral agents.

In another embodiment, a pharmaceutical composition of the present invention comprises one or more compounds of the present invention (or salts thereof), and one or more other anti-HCV agents. For example, a pharmaceutical composition of the present invention can comprise a compound(s) of the present invention having Formula I, II, III or IV (or a salt thereof), and an agent selected from HCV polymerase inhibitors (including nucleoside or non-nucleoside type of polymerase inhibitors), HCV protease inhibitors, HCV helicase inhibitors, CD81 inhibitors, cyclophilin inhibitors, IRES inhibitors, or NS5A inhibitors.

In yet another embodiment, a pharmaceutical composition of the present invention comprises one or more compounds of the present invention (or salts thereof), and one or more other antiviral agents, such as anti-HBV, anti-HIV agents, or anti-hepatitis A, anti-hepatitis D, anti-hepatitis E or anti-hepatitis G agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, or other HIV protease, reverse transcriptase, integrase or fusion inhibitors. Any other desirable antiviral agents can also be included in a pharmaceutical composition of the present invention, as appreciated by those skilled in the art in light of the present invention.

In another embodiment, the invention provides a pharmaceutical composition further comprising pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

In yet another embodiment, the compounds or pharmaceutical compositions of the invention are administered with ritonavir, either simultaneously or sequentially. In certain embodiments, a compound or a pharmaceutical composition of the invention is administered in the same composition as ritonavir. In another embodiment, a compound or a pharmaceutical composition thereof of the invention is administered in a different composition than ritonavir.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

Any compound described herein, or a pharmaceutically acceptable salt thereof, can be used to prepared pharmaceutical compositions of the present invention.

The present invention further features methods of using the compounds of the present invention (or salts thereof) to inhibit HCV replication. The methods comprise contacting cells infected with HCV virus with an effective amount of a compound of the present invention (or a salt thereof), thereby inhibiting the replication of HCV virus in the cells. As used herein, "inhibiting" means significantly reducing, or abolishing, the activity being inhibited (e.g., viral replication). In many cases, representative compounds of the present invention can reduce the replication of HCV virus (e.g., in an HCV replicon assay as described above) by at least 10%, 20%, 30%, 40%, 50%, 60%, 70%, 80%, 90%, 95% or more.

The compounds of the present invention may inhibit one or more HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c or 3a. In one embodiment, a compound or compounds of the present invention (or salts thereof) are used to inhibit the replication of HCV genotype 1a. In another embodiment, a compound or compounds of the present invention (or salts thereof) are used to inhibit the replication of HCV genotype 1b. In still another embodiment, a compound or compounds of the present invention (or salts thereof) are used to inhibit the replication of both HCV genotypes 1a and 1b.

The present invention also features methods of using the compounds of the present invention (or salts thereof) to treat HCV infection. The methods typically comprise administering a therapeutic effective amount of a compound of the present invention (or a salt thereof), or a pharmaceutical composition comprising the same, to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts thereof), or a pharmaceutical composition comprising the same, to an HCV patient, thereby reducing the HCV viral level in the blood or liver of the patient.

A compound of the present invention (or a salt thereof) can be administered as the sole active pharmaceutical agent, or in combination with another desired drug, such as other anti-HCV agents, anti-HIV agents, anti-HBV agents, anti-hepatitis A agents, anti-hepatitis D agents, anti-hepatitis E agents, anti-hepatitis G agents, or other antiviral drugs. Any compound described herein, or a pharmaceutically acceptable salt thereof, can be employed in the methods of the present invention.

A compound of the present invention (or a salt thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The present invention further features methods of using the pharmaceutical compositions of the present invention to treat HCV infection. The methods typically comprise administering a pharmaceutical composition of the present invention to an HCV patient, thereby reducing the HCV viral level in the blood or liver of the patient. Any pharmaceutical composition described herein can be used in the methods of the present invention.

In addition, the present invention features use of the compounds or salts of the present invention for the manufacture of medicaments for the treatment of HCV infection. Any compound described herein, or a pharmaceutically acceptable salt thereof, can be used to make medicaments of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses, either with or without a cytochrome P450 monooxygenase inhibitor such as ritonavir. The suitable daily dose for the co-administered cytochrome P450 monooxygenase inhibitor (e.g., ritonavir) can range, without limitation, from 10 to 200 mg. Preferably, a compound(s) of the present invention, or a combination of a compound(s) of the invention and ritonavir, is administered once daily or twice daily to achieve the desired daily dose amount. For instance, when used without ritonavir, a compound of the present invention can be administered to a patient twice a day with a total daily dose of 200, 400, 600, 800, 1000, 2000, 3000, 4000, 4200, 4400, 4600, 4800 or 5000 mg. For another instance, when used in combination with ritonavir, a compound of the present invention can be administered to a patient once or twice a day with a total daily dose of 200, 400, 600 or 800 mg, where the amount of ritonavir can be 25, 50 or 100 mg per administration.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed:

1. The compound tert-butyl(2R,6S,13aS,14aR,16aS,Z)-14a-(cyclopropylsulfonylcarbamoyl)-5,16-dioxo-2-(1,2,3,4-tetrahydrophenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate, or a pharmaceutically acceptable salt thereof

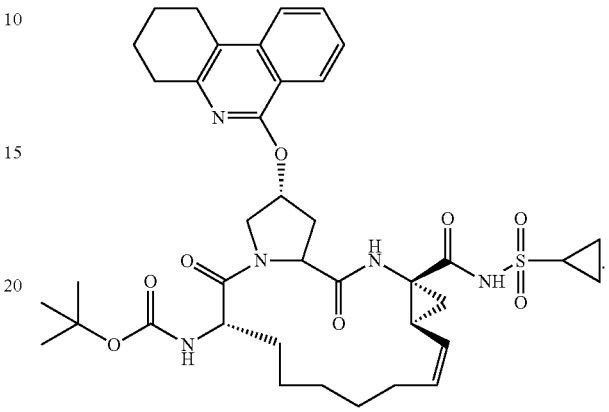

2. A pharmaceutical composition comprising an effective amount of tert-butyl(2R,6S,13aS,14aR,16aS,Z)-14a-(cyclopropylsulfonylcarbamoyl)-5,16-dioxo-2-(1,2,3,4-tetrahydrophenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate or a pharmaceutically acceptable salt thereof

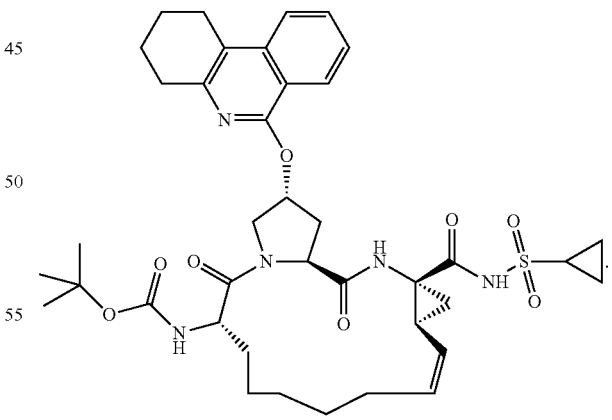

3. A compound or a pharmaceutically acceptable salt thereof, wherein said compound is selected from the group consisting of:

tert-butyl(2R,6S,13aS,14aR,16aS,Z)-14a-(cyclopropyl-
sulfonylcarbamoyl)-5,16-dioxo-2-(7,8,9,10-tetrahy-
drophenanthridin-6-yloxy)-1,2,3,5,6,7,8,9,10,11,13a,
14,14a,15,16,16a-hexadecahydrocyclopropa[e]pyrrolo
[1,2-a][1,4]diazacyclopentadecin-6-ylcarbamate,

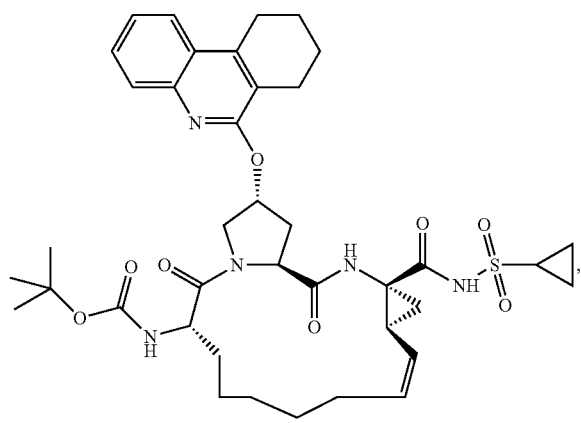

tert-butyl(2R,6S,13aS,14aR,16aS,Z)-14a-(cyclopropyl-
sulfonylcarbamoyl)-2-(2-methoxy-7,8,9,10-tetrahydro-
phenanthridin-6-yloxy)-5,16-dioxo-1,2,3,5,6,7,8,9,10,
11,13a,14,14a,15,16,16a-hexadecahydrocyclopropa[e]
pyrrolo[1,2-a][1,4]diazacyclopentadecin-6-
ylcarbamate,

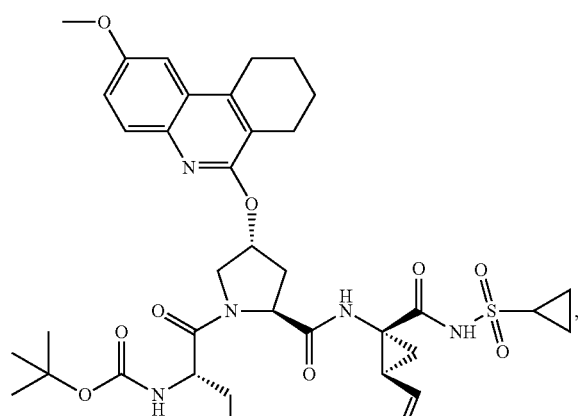

tert-butyl(2R,6S,13aS,14aR,16aS,Z)-14a-(cyclopropyl-
sulfonylcarbamoyl)-2-(2,3-dihydro-1H-cyclopenta[c]
quinolin-4-yloxy)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-
ylcarbamate,

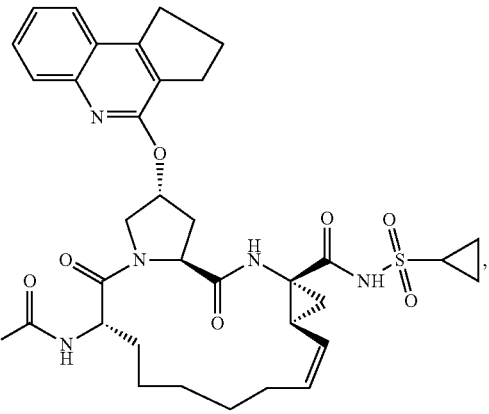

tert-butyl(2R,6S,13aS,14aR,16aS,Z)-14a-(cyclopropyl-
sulfonylcarbamoyl)-2-(6-fluoro-2,3-dihydro-1H-cyclo-
penta[c]quinolin-4-yloxy)-5,16-dioxo-1,2,3,5,6,7,8,9,
10,11,13a,14,14a,15,16,16a-hexadecahydrocyclopropa
[e]pyrrolo[1,2-a][1,4]diazacyclopentadecin-6-
ylcarbamate, tert-butyl(2R,6S,13aS,14aR,16aS,Z)-14a-(cyclopropyl-
sulfonylcarbamoyl)-2-(2,3-dihydrofuro[3,2-c]quino-
lin-4-yloxy)-5,16-dioxo-1,2,3,5,6,7,8,9,10,11,13a,14,
14a,15,16,16a-hexadecahydrocyclopropa[e]pyrrolo[1,
2-a][1,4]diazacyclopentadecin-6-ylcarbamate,

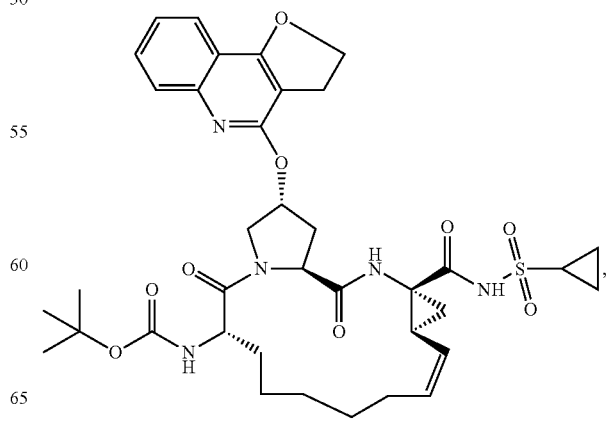

67 tert-butyl(2R,6S,13aS,14aR,16aS,Z)-14a-(cyclopropyl-
sulfonylcarbamoyl)-5,16-dioxo-2-(1,2,3,4-tetrahydro-
phenanthridin-6-yloxy)-1,2,3,5,6,7,8,9,10,11,13a,14,
14a,15,16,16a-hexadecahydrocyclopropa[e]pyrrolo[1,
2-a][1,4]diazacyclopentadecin-6-ylcarbamate,

68

11,13a,14,14a,15,16,16a-hexadecahydrocyclopropa[e]
pyrrolo[1,2-a][1,4]diazacyclopentadecin-6-
ylcarbamate,

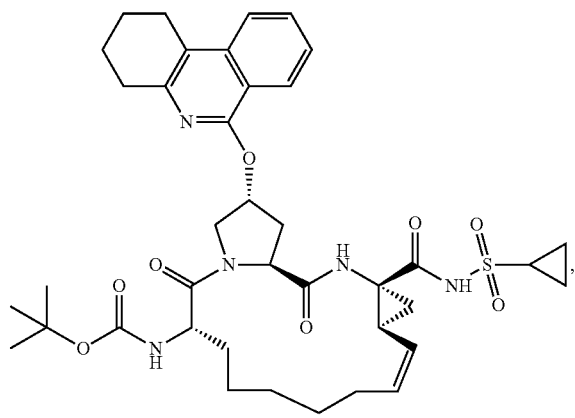

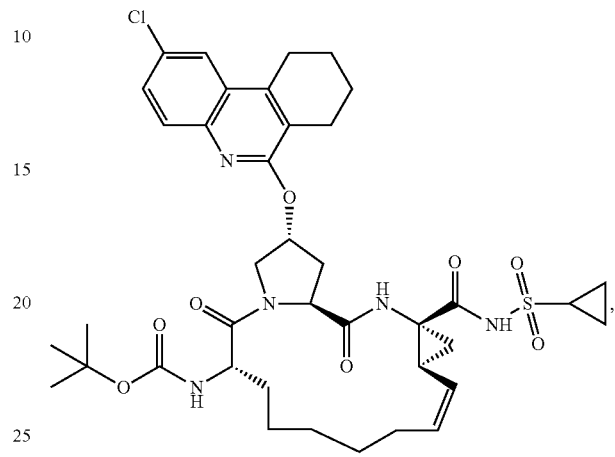

tert-butyl(2R,6S,13aS,14aR,16aS,Z)-14a-(cyclopropyl-
sulfonylcarbamoyl)-2-(2,3-dihydro-1H-cyclopenta[c]
isoquinolin-5-yloxy)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-
ylcarbamate, tert-butyl(2R,6S,13aS,14aR,16aS,Z)-14a-(cyclopropyl-
sulfonylcarbamoyl)-2-(8-methoxy-2,3-dihydro-1H-cy-
clopenta[c]quinolin-4-yloxy)-5,16-dioxo-1,2,3,5,6,7,8,
9,10,11,13a,14,14a,15,16,16a-
hexadecahydrocyclopropa[e]pyrrolo[1,2-a][1,4]
diazacyclopentadecin-6-ylcarbamate,

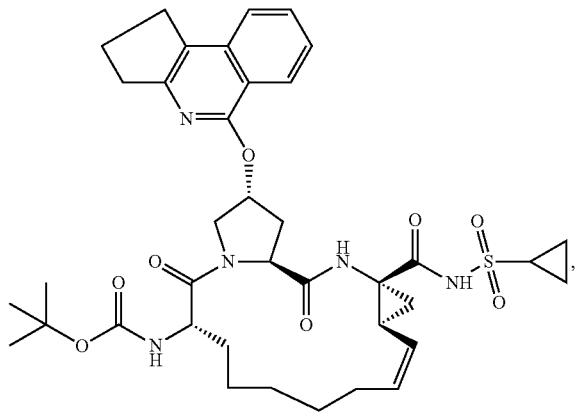

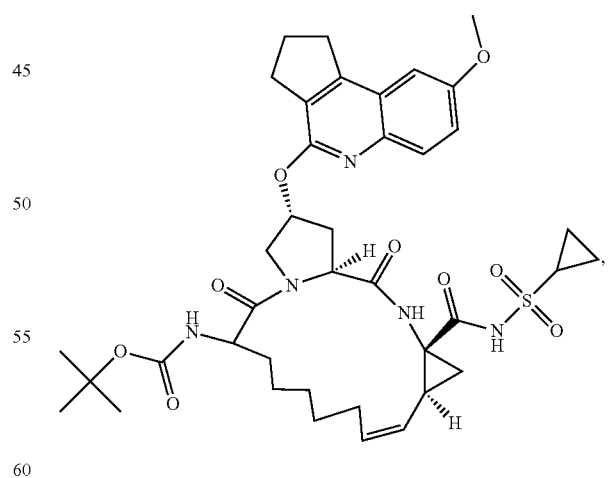

tert-butyl(2R,6S,13aS,14aR,16aS,Z)-2-(2-chloro-7,8,9,
10-tetrahydrophenanthridin-6-yloxy)-14a-(cyclopro-
pylsulfonylcarbamoyl)-5,16-dioxo-1,2,3,5,6,7,8,9,10, tert-butyl (2R,6S,13aS,14aR,16aS,Z)-2-(benzo[c][1,8]
naphthyridin-6-yloxy)-14a-(cyclopropylsulfonylcar-
bamoyl)-5,16-dioxo-1,2,3,5,6,7,8,9,10,11,13a,14,14a, 15,16,16a-hexadecahydrocyclopropa[e]pyrrolo[1,2-a][1,4]diazacyclopentadecin-6-ylcarbamate, hexadecahydrocyclopropa[e]pyrrolo[1,2-a][1,4]diazacyclopentadecine-14a-carboxamide,

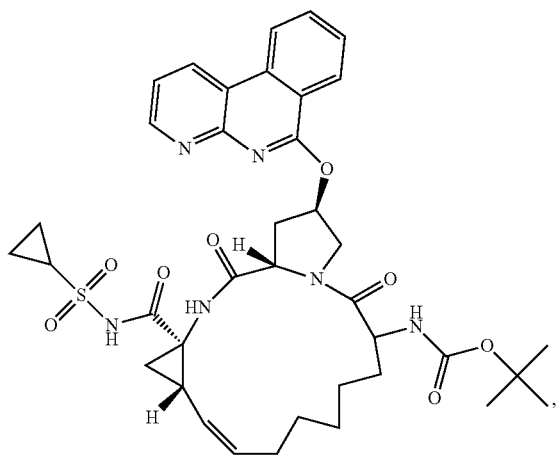

(2R,6S,13aS,14aR,16aS,Z)-2-(benzo[c][1,8]naphthyridin-6-yloxy)-N-(cyclopropylsulfonyl)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide,

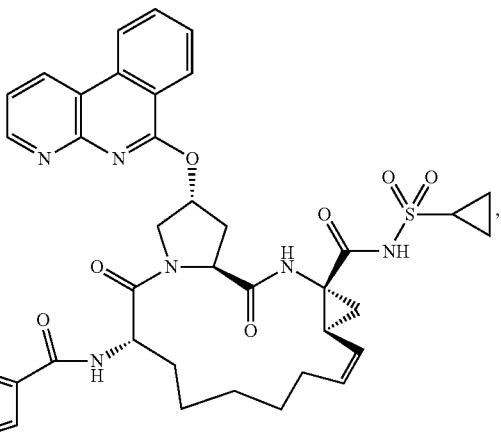

N-((2R,6S,13aS,14aR,16aS,Z)-2-(benzo[c][1,8]naphthyridin-6-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide,

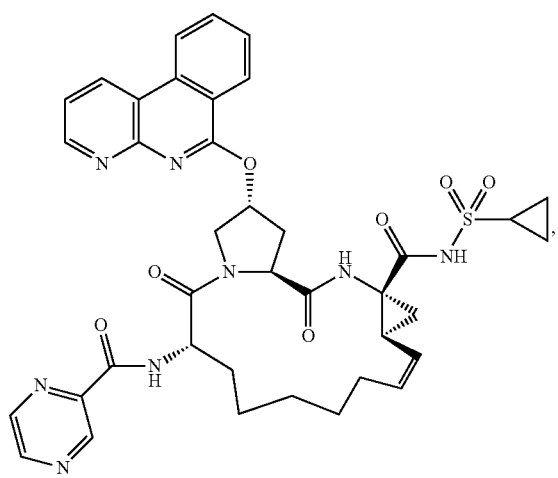

(2R,6S,13aS,14aR,16aS,Z)-2-(benzo[c][1,8]naphthyridin-6-yloxy)-N-(cyclopropylsulfonyl)-6-(5-methyl-1H-pyrazole-3-carboxamido)-5,16-dioxo-1,2,3,5,6,7,8,9,10,11,13a,14,14a,15,16,16a-

(2R,6S,13aS,14aR,16aS,Z)-2-(benzo[c][1,8]naphthyridin-6-yloxy)-N-(cyclopropylsulfonyl)-6-(5-methylpyrazine-2-carboxamido)-5,16-dioxo-1,2,3,5,6,7,8,9,10,11,13a,14,14a,15,16,16a-

| 71 | 72 |
|---|---|
| hexadecahydrocyclopropa-[e]pyrrolo[1,2-a][1,4]diazacyclopentadecine-14a-carboxamide, | 15,16,16a-hexadecahydrocyclopropa[e]pyrrolo[1,2-a][1,4]diazacyclopentadecine-14a-carboxamide, |

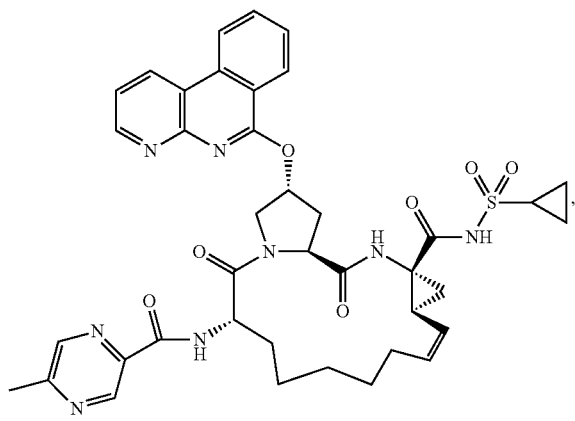 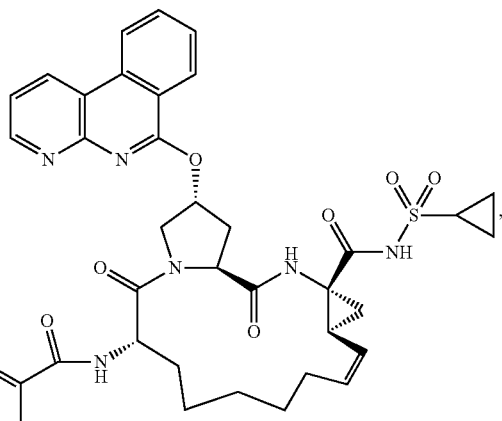

N-((2R,6S,13aS,14aR,16aS,Z)-2-(benzo[c][1,8]naphthyridin-6-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-5-carboxamide, (2R,6S,13aS,14aR,16aS,Z)-2-(benzo[c][1,8]naphthyridin-6-yloxy)-N-(cyclopropylsulfonyl)-5,16-dioxo-6-(pyridazine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide,

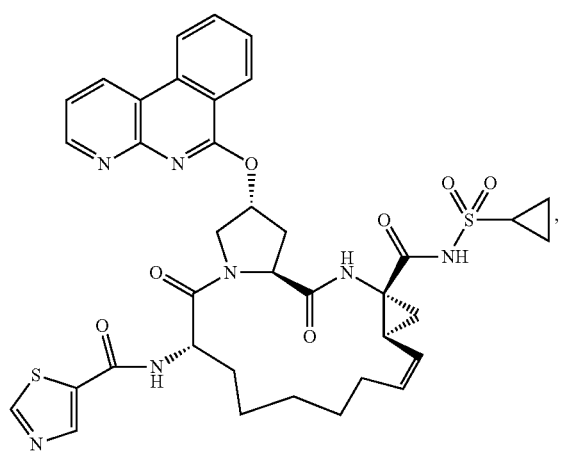 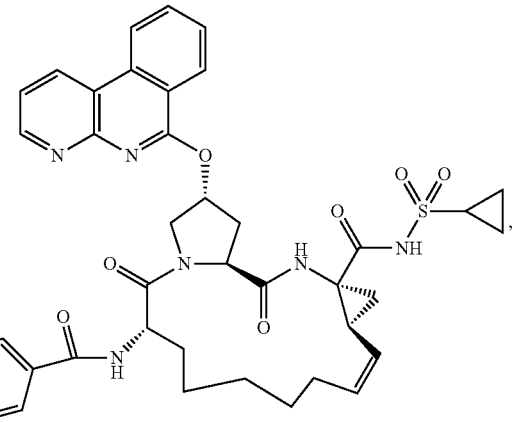

(2R,6S,13aS,14aR,16aS,Z)-2-(benzo[c][1,8]naphthyridin-6-yloxy)-N-(cyclopropylsulfonyl)-6-(2-fluorobenzamido)-5,16-dioxo-1,2,3,5,6,7,8,9,10,11,13a,14,14a, (2R,6S,13aS,14aR,16aS,Z)-2-(benzo[c][1,8]naphthyridin-6-yloxy)-N-(cyclopropylsulfonyl)-5,16-dioxo-6-(pyrimidine-4-carboxamido)-1,2,3,5,6,7,8,9,10,11,13a, 14,14a,15,16,16a-hexadecahydrocyclopropa[e]pyrrolo[1,2-a][1,4]diazacyclopentadecine-14a-carboxamide, 5,6,7,8,9,10,11,13a,14,14a,15,16,16a-hexadecahydrocyclopropa[e]pyrrolo[1,2-a][1,4]diazacyclopentadecine-14a-carboxamide,

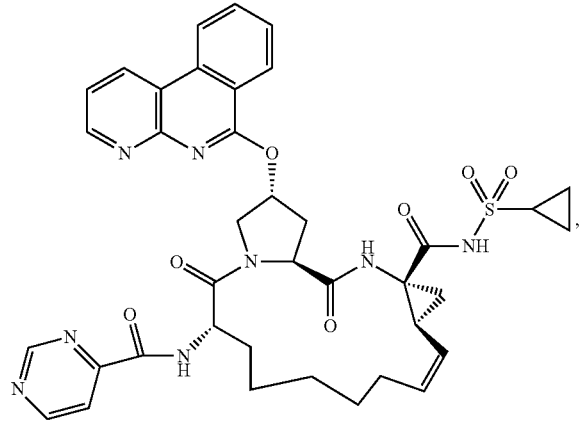

(2R,6S,13aS,14aR,16aS,Z)-2-(benzo[c][1,8]naphthyridin-6-yloxy)-N-(cyclopropylsulfonyl)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide,

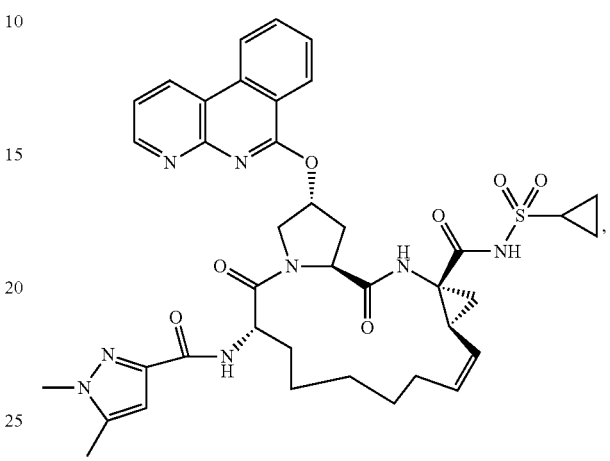

tert-butyl (2R,6S,13aS,14aR,16aS,Z)-14a-(cyclopropylsulfonylcarbamoyl)-5,16-dioxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate,

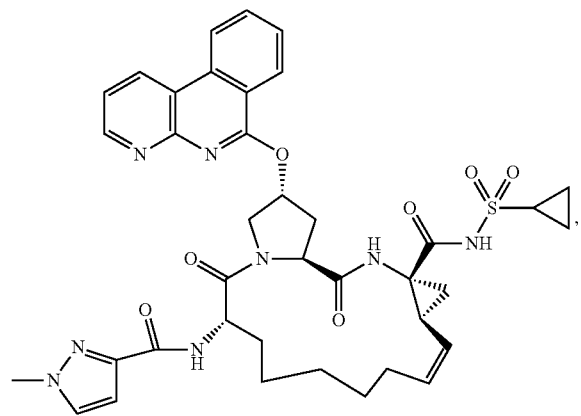

(2R,6S,13aS,14aR,16aS,Z)-2-(benzo[c][1,8]naphthyridin-6-yloxy)-N-(cyclopropylsulfonyl)-6-(1,5-dimethyl-1H-pyrazole-3-carboxamido)-5,16-dioxo-1,2,3,

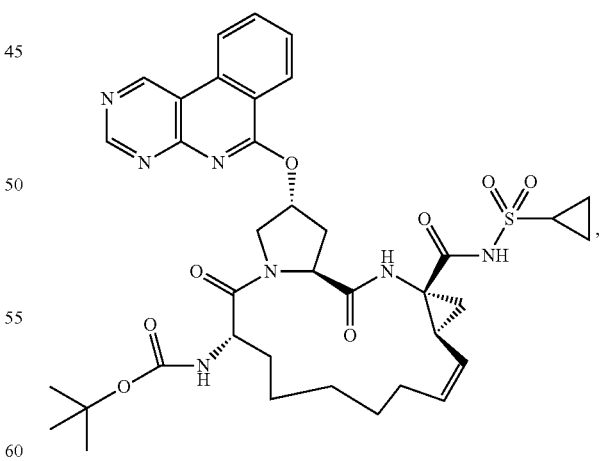

2R,6S,13aS,14aR,16aS,Z)-N-(cyclopropylsulfonyl)-5,16-dioxo-6-(pyrazine-2-carboxamido)-2-(pyrimido[4, 5-c]isoquinolin-6-yloxy)-1,2,3,5,6,7,8,9,10,11,13a,14,
14a,15,16,16a-hexadecahydrocyclopropa[e]pyrrolo[1,
2-a][1,4]diazacyclopentadecine-14a-carboxamide, 16,16a-hexadecahydrocyclopropa[e]pyrrolo[1,2-a][1,
4]diazacyclopentadecin-6-yl)-5-methylisoxazole-3-
carboxamide,

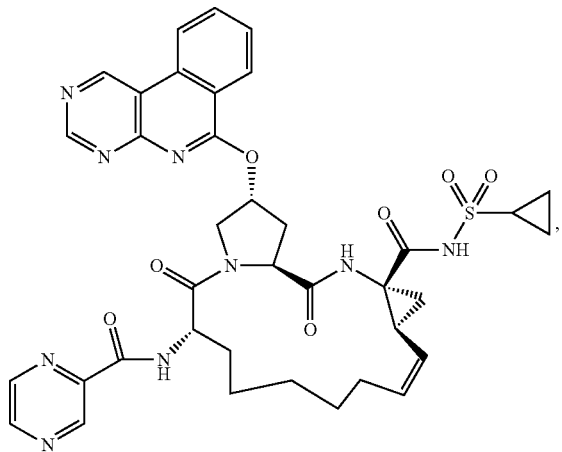

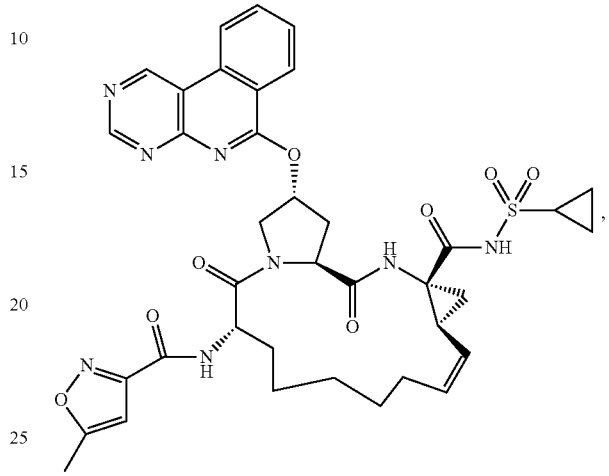

(2R,6S,13aS,14aR,16aS,Z)-N-(cyclopropylsulfonyl)-6-
(5-methyl-1H-pyrazole-3-carboxamido)-5,16-dioxo-2-
(pyrimido[4,5-c]isoquinolin-6-yloxy)-1,2,3,5,6,7,8,9,
10,11,13a,14,14a,15,16,16a-hexadecahydrocyclopropa
[e]pyrrolo[1,2-a][1,4]diazacyclopentadecine-14a-
carboxamide, (2R,6S,13aS,14aR,16aS,Z)-N-(cyclopropylsulfonyl)-6-
(5-methylpyrazine-2-carboxamido)-5,16-dioxo-2-(py-
rimido[4,5-c]isoquinolin-6-yloxy)-1,2,3,5,6,7,8,9,10,
11,13a,14,14a,15,16,16a-hexadecahydrocyclopropa[e]
pyrrolo[1,2-a][1,4]diazacyclopentadecine-14a-
carboxamide,

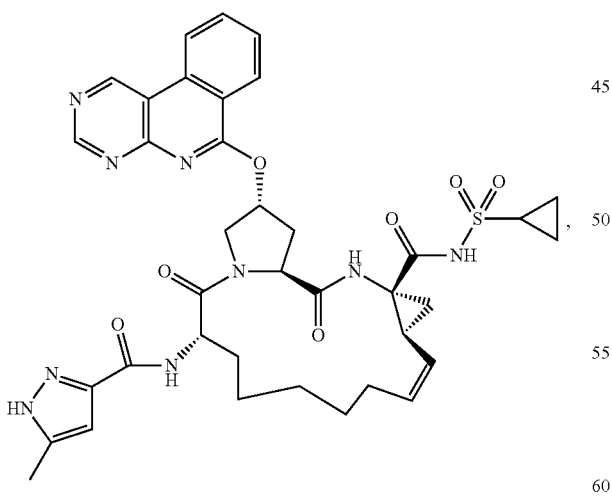

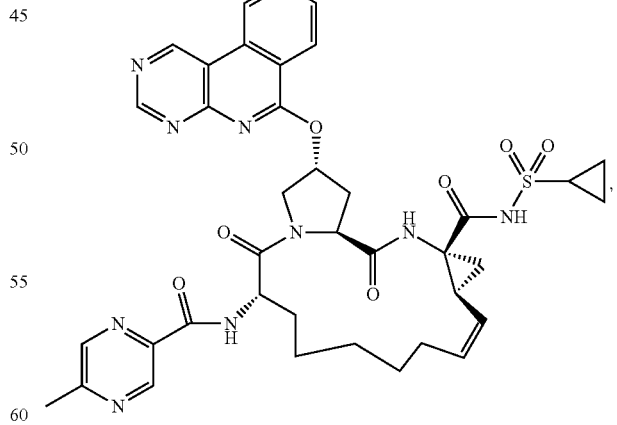

N-((2R,6S,13aS,14aR,16aS,Z)-14a-(cyclopropylsulfo-
nylcarbamoyl)-5,16-dioxo-2-(pyrimido[4,5-c]iso-
quinolin-6-yloxy)-1,2,3,5,6,7,8,9,10,11,13a,14,14a,15, N-((2R,6S,13aS,14aR,16aS,Z)-14a-(cyclopropylsulfo-
nylcarbamoyl)-5,16-dioxo-2-(pyrimido[4,5-c]iso-

77 quinolin-6-yloxy)-1,2,3,5,6,7,8,9,10,11,13a,14,14a,15,
16,16a-hexadecahydrocyclopropa[e]pyrrolo[1,2-a][1,
4]diazacyclopentadecin-6-yl)thiazole-5-carboxamide,

78

14,14a,15,16,16a-hexadecahydrocyclopropa[e]pyrrolo
[1,2-a][1,4]diazacyclopentadecine-14a-carboxamide,

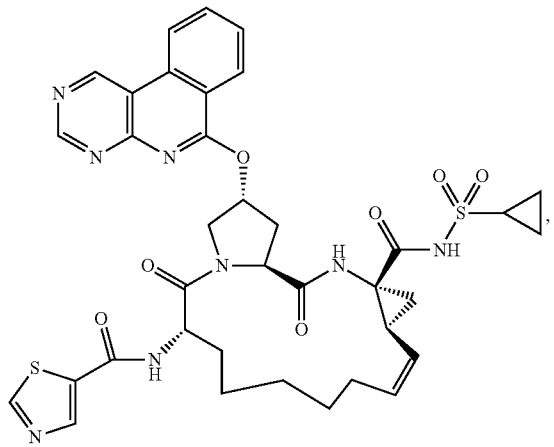

(2R,6S,13aS,14aR,16aS,Z)-N-(cyclopropylsulfonyl)-6-
(2-fluorobenzamido)-5,16-dioxo-2-(pyrimido[4,5-c]
isoquinolin-6-yloxy)-1,2,3,5,6,7,8,9,10,11,13a,14,14a,
15,16,16a-hexadecahydrocyclopropa[e]pyrrolo[1,2-a]
[1,4]diazacyclopentadecine-14a-carboxamide,

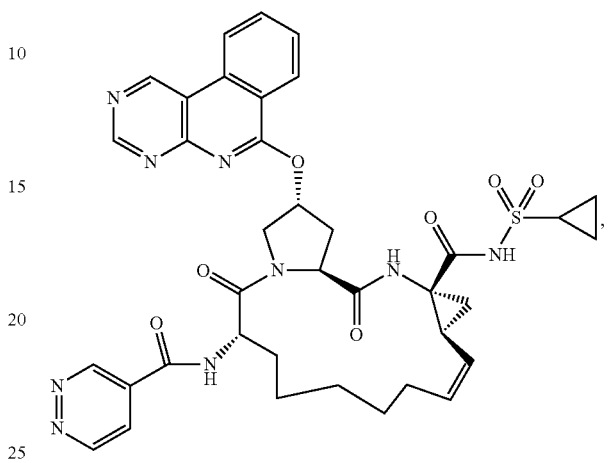

(2R,6S,13aS,14aR,16aS,Z)-N-(cyclopropylsulfonyl)-5,
16-dioxo-6-(pyrimidine-4-carboxamido)-2-(pyrimido
[4,5-c]isoquinolin-6-yloxy)-1,2,3,5,6,7,8,9,10,11,13a,
14,14a,15,16,16a-hexadecahydrocyclopropa[e]pyrrolo
[1,2-a][1,4]diazacyclopentadecine-14a-carboxamide,

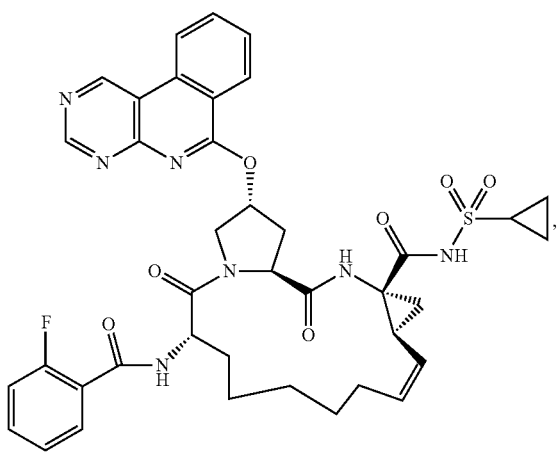

(2R,6S,13aS,14aR,16aS,Z)-N-(cyclopropylsulfonyl)-5,
16-dioxo-6-(pyridazine-4-carboxamido)-2-(pyrimido
[4,5-c]isoquinolin-6-yloxy)-1,2,3,5,6,7,8,9,10,11,13a,

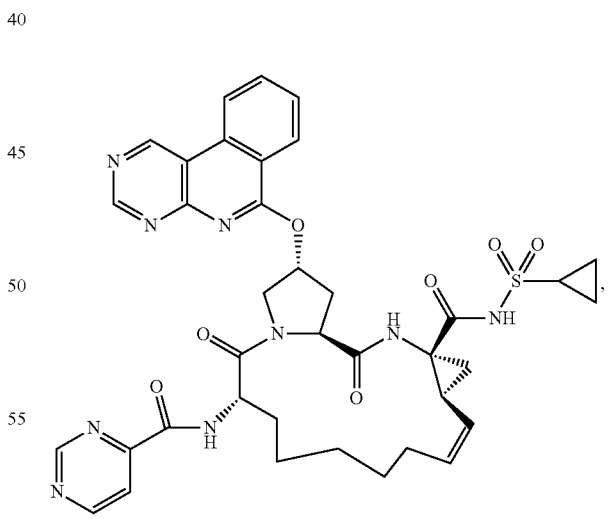

(2R,6S,13aS,14aR,16aS,Z)-N-(cyclopropylsulfonyl)-6-
(1-methyl-1H-pyrazole-3-carboxamido)-5,16-dioxo-2-
(pyrimido[4,5-c]isoquinolin-6-yloxy)-1,2,3,5,6,7,8,9,

79
10,11,13a,14,14a,15,16,16a-hexadecahydrocyclopropa[e]pyrrolo[1,2-a][1,4]diazacyclopentadecine-14a-carboxamide,
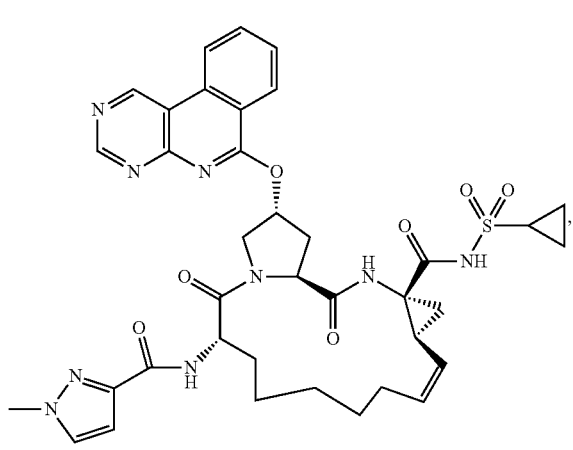
and
(2R,6S,13aS,14aR,16aS,Z)-N-(cyclopropylsulfonyl)-6-(1,5-dimethyl-1H-pyrazole-3-carboxamido)-5,16-di-
80
oxo-2-(pyrimido[4,5-c]isoquinolin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide
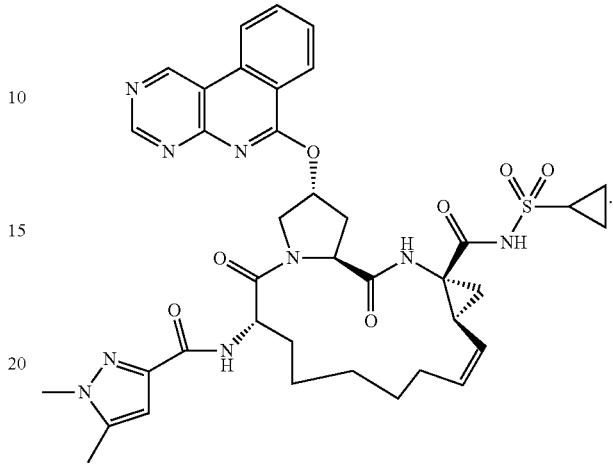
\* \* \* \* \*